US006780883B2

(12) United States Patent
Booth et al.

(10) Patent No.: US 6,780,883 B2
(45) Date of Patent: Aug. 24, 2004

(54) AMIDE INHIBITORS OF MICROSOMAL TRIGLYCERIDE TRANSFER PROTEIN

(75) Inventors: Richard John Booth, Ann Arbor, MI (US); Helen Tsenwhei Lee, Ann Arbor, MI (US); Jason Keith Pontrello, Kalamazoo, MI (US); Randy Ranjee Ramharack, Ann Arbor, MI (US); Bruce David Roth, Plymouth, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/021,633

(22) Filed: Dec. 12, 2001

(65) Prior Publication Data

US 2002/0156281 A1 Oct. 24, 2002

Related U.S. Application Data

(63) Continuation-in-part of application No. 09/422,568, filed on Oct. 21, 1999, now abandoned.
(60) Provisional application No. 60/107,119, filed on Nov. 5, 1998.

(51) Int. Cl.$^7$ ........................ A61K 31/44; C07D 213/74
(52) U.S. Cl. ........................................ 514/352; 546/309
(58) Field of Search .......................... 514/352; 546/309

(56) References Cited

U.S. PATENT DOCUMENTS

| | | | | |
|---|---|---|---|---|
| 3,624,096 A | * | 11/1971 | Abramovitch, VI et al. | ............ 260/294.9 |
| 4,124,370 A | | 11/1978 | Yu | |
| 4,180,670 A | | 12/1979 | Edington et al. | |
| 4,855,308 A | * | 8/1989 | Kester et al. | ............ 514/332 |
| 5,453,432 A | * | 9/1995 | Wagner et al. | ............ 514/344 |
| 5,595,872 A | | 1/1997 | Wetterau et al. | |
| 5,712,279 A | | 1/1998 | Biller et al. | |
| 5,739,135 A | | 4/1998 | Biller et al. | |
| 5,760,246 A | | 6/1998 | Biller et al. | |

FOREIGN PATENT DOCUMENTS

| | | | |
|---|---|---|---|
| FR | 7699 | * | 2/1970 |
| JP | 55031099 | | 3/1980 |
| WO | WO 98/09630 | * | 3/1988 |
| WO | WO 9748694 | | 12/1997 |

OTHER PUBLICATIONS

Deyanov et al, "Synthesis of 1–aryl–7–methyl, etc" CA 115 : 279952 (1991).*
Buchiesi et al, "Evaluation of the polar–inductive, etc" CA 108 : 130898 (1988).*
Moerkver, "Structure of Carbamoylaten, etc" CA 106 : 156246 (1987).*
Shramm et al, "Synthesis and Properties, etc" CA 102 : 166694 (1985).*
Abramovitch et al I, "Direct Acylamination, etc" J. Org. Chem. 1983, 48, 4391–4393.*

Peterson et al, "Imidazo [1,2–a] Pyridine, etc" CA 95 : 169072 (1981).*
Shell, "Heterocyclic Compounds with Fungicidal, etc" CA 95 : 97849 (1981).*
Abramovitch et al II, "Direct Side–Chain, etc" CA 92 : 146559 (1980).*
Abramovitch et al III, "Direct Acylamination, etc" J. Org. Chem., 39 (13), 1974, 1795–1802.*
Abramovitch et al IV; "Direct Side Chain Amination, etc" CA 84 : 74053 (1976).*
Abramovitch et al V, "Direct Acylamination of, etc" J. Org. Chem., 39 (13), 1974, 1802–1807.*
Gordon, David A., Lipidology, "Recent Advances In Elucidating the Role of the Microsomal Triglyceride Transfer Protein In Apolipoprotein B Lipoprotein Assembly", 1997, vol. 8: 131–137.
Wetterau, J.R., BBA 1345, "Microsomal Triglyceride Transfer Protein", 1997, PP 136–150.
Jamil, Haris,et al., Proc.Natl. Acad. Sci, Usa, An Inhibitor of the Microsomal Triglyceride Transfer Protein Inhibits Apob Secretion from HepG2 Cells, 1996, 93: 11991–11995.
Berge, S.M., et al, Pharmaceutical Salts, J. Pharm. Sci, 1977; 66: 1–19.
T. Higuchi & V. Stella, Pro–drugs as Novel Delivery Systems, vol. 14 of the A.C.S. Symposium Series.
Roche, Edward B., Bioreversible Carriers in Drug Design, American Pharmaceutical Association & Pergamon Press, 1987.
Ghosh, Somnath, et al, Studies on Enamides, Part–5: A Novel Pathway for Photochemical Reaction of N–1–Cyclohexenyl–N–Phenylarylamides, Tetrahedron Lett., 1996; 37(18):3169–3170.
Yasuo Kikugawa, et al., AlCl3–mediated Regioselective Migration of a Methoxy Group of N–Methoxy–N–Phenylamides to the ortho Position of the Phenyl Ring, J. of Soc., Chem. Commun., 1989; 19:1450–1451.
J. Mirek, et al., Thin–layer chromatography of anilides of pyridinecarboxylic acids and benz–amidopyridines, Journal of Chromatograph, 1979, 171:462–465.

(List continued on next page.)

*Primary Examiner*—Patricia L. Morris
(74) *Attorney, Agent, or Firm*—Michelle A. Sherwood

(57) ABSTRACT

The present invention provides compounds having the Formula I

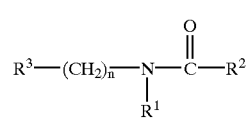

The present invention also provides pharmaceutical compositions comprising a compound of Formula I and methods of treatment of atherosclerosis, obesity, restenosis, coronary heart disease, hyperlipoproteinemia, hypercholesterolemia, and hypertriglyceridemia.

8 Claims, No Drawings

OTHER PUBLICATIONS

S. Oae, et al., A Novel Cyclization Reaction Of o–Carboxyphenyl and o–Carbamoylphenyl Sulfoxides: Formation of Benzoxathiane, Dihydrobenzothiazine and Benxoisothiazoline Derivatives, Tetrahedron, 1974, 30: 2641–2646.

Katritzky, Alan, The Chemistry of N–Substituted Bernzotriazoles, Part 20, Mono–N–t–Butylation of Aromatic and Heteroaromatic Amines, J. Chem. Soc. Perkin Trans., 1989, 3: 639–642.

Vladimir Valenta, Potential Nootropic Agents: Synthesis of Some (2–Oxo–1–Pyrrolidinyl)Acetamides and Some Related Compounds, Collect, Czech. Chem. Commun., 1990, 55: 2756–2764.

Cadogan, et al., Gas Phase Generation and Cyclisation Reactions of Some o–Substituted Phenyl Radicals, Tetrahedron, 1992, 48, 36: 7747–7762.

* cited by examiner

AMIDE INHIBITORS OF MICROSOMAL TRIGLYCERIDE TRANSFER PROTEIN

CROSS REFERENCED TO RELATED APPLICATION

This is a continuation-in-part of U.S. application Ser. No. 09/422,568 filed on Oct. 21, 1999, now abandoned, which claims benefit of priority from U.S. Provisional Application No. 60/107,119 filed on Nov. 5, 1998.

FIELD OF THE INVENTION

The present invention relates to compounds that are inhibitors of the microsomal triglyceride transfer protein. The invention also relates to methods of treatment of atherosclerosis, obesity, restenosis, coronary heart disease, hyperlipoproteinemia, hypercholesterolemia, and hypertriglyceridemia, and to pharmaceutical compositions containing the inhibitors.

BACKGROUND OF THE INVENTION

The microsomal triglyceride transfer protein (MTP) is required for the assembly of lipoproteins containing apolipoprotein B (apoB). Examples of lipoproteins that contain apoB, include chylomicrons, very low density lipoproteins (VLDL), intermediate density lipoproteins (IDL), high density lipoproteins (HDL), low density lipoproteins (LDL), and lipoprotein a [Lp(a)]. MTP is a heterodimer composed of a unique large subunit of 97 kDA and an ubiquitous multifunctional protein called protein disulfide isomerase.

The function of MTP has been discovered, in part, through the investigation of the disease abetalipoproteinemia, which is a rare autosomal recessive disease that is characterized by defective apoB lipoprotein assembly and secretion. Studies have now shown that persons having abetalipoproteinemia have mutations in the MTP large subunit gene. As a result of this mutation, persons afflicted with abetalipoproteinemia have only trace levels of apoB in plasma and total plasma levels of cholesterol of about 40 mg/dL.

Abnormal plasma lipid and/or lipoprotein concentrations plays a role in diseases such as atherosclerosis, obesity, restenosis, coronary heart disease, hyperlipoproteinemia, hypercholesterolemia, and hypertriglyceridemia. Thus, it would be beneficial to obtain compounds that can inhibit MTP.

U.S. Pat. Nos. 5,712,279 and 5,739,135, which are hereby incorporated by reference in their entirety, relate to compounds that inhibit MTP. The compounds disclosed in these patents are structurally different from the compounds of the present invention.

SUMMARY OF THE INVENTION

The present invention provides compounds having the Formula I

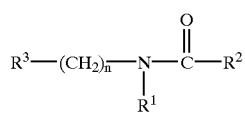

wherein $R^1$ is pyridyl, —$CH_2$-pyridyl, substituted pyridyl, —$CH_2$-substituted pyridyl, phenyl, substituted phenyl,

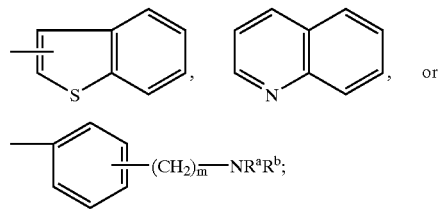

each $R^a$ and $R^b$ are independently hydrogen or $C_1$–$C_6$ alkyl;

m is 0 to 4;

n is 0, 1, or 2;

$R^2$ is substituted phenyl, phenyl,

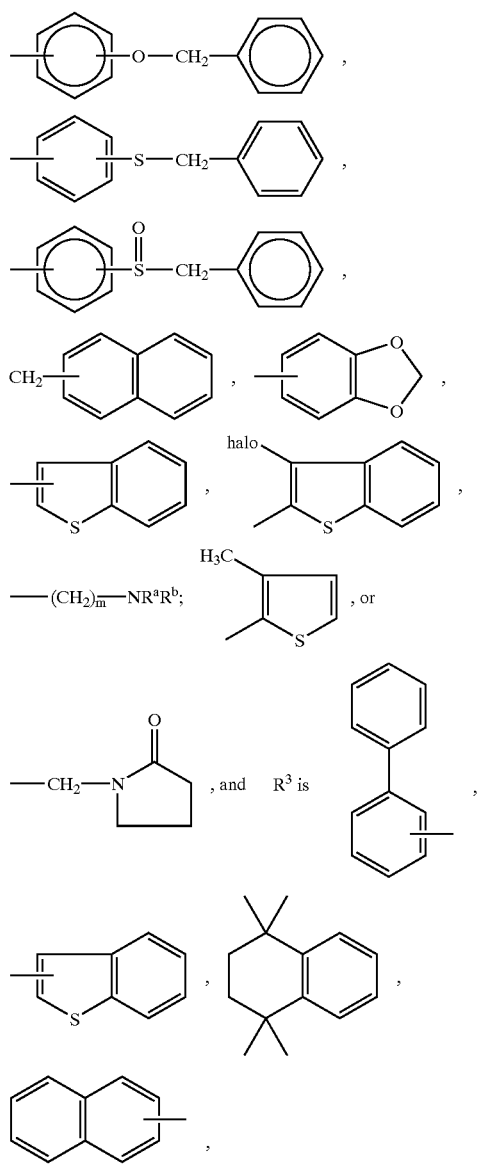

phenyl or substituted phenyl, a pharmaceutically acceptable salt thereof.

In a preferred embodiment of the compounds of Formula I,

R³ is 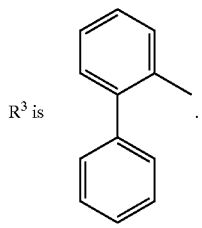.

In another preferred embodiment of the compounds of Formula I,

R³ is

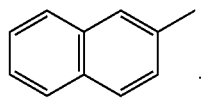.

In another preferred embodiment of the compounds of Formula I, R¹ is pyridyl, or —CH₂-pyridyl.

In another preferred embodiment of the compounds of Formula I, R¹ is substituted phenyl or substituted pyridyl.

In another preferred embodiment of the compounds of Formula I, R² is substituted phenyl, or phenyl.

In another preferred embodiment, the present invention provides compounds having the Formula I

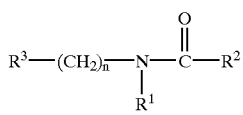

wherein

R¹ is pyridyl, substituted phenyl, phenyl
—CH₂-pyridyl,

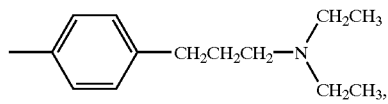

substituted pyridyl, or

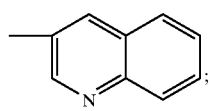;

R² is substituted phenyl, phenyl,

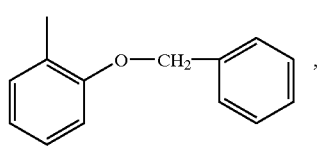

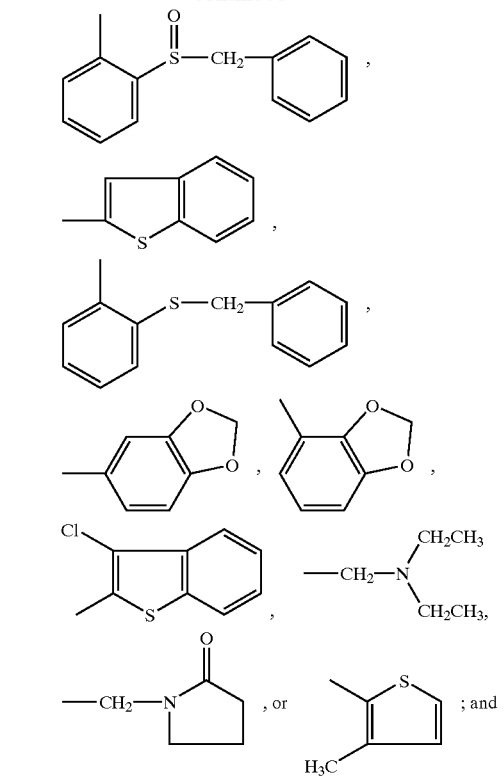

substituted phenyl, or the pharmaceutically acceptable salt thereof.

In a more preferred embodiment of the compounds of Formula I, the present invention provides the compounds:

2-Benzylsulfanyl-N-(4-methoxy-benzyl)-N-(4-methoxy-phenyl)-benzamide;
N-(3,5-Di-tert-butyl-benzyl)-3,4-dimethoxy-N-phenyl-benzamide;
N-(3,5-Bis-trifluoromethyl-benzyl)-3,4-dimethoxy-N-phenyl-benzamide;
N-(3,5-Dibromo-benzyl)-3,4-dimethoxy-N-phenyl-benzamide;
3,4-Dimethoxy-N-(4-methoxy-benzyl)-N-phenyl-benzamide;
3,4-Dimethoxy-N-(3-methoxy-benzyl)-N-phenyl-benzamide;
N-(3,4-Dichloro-benzyl)-3,4-dimethoxy-N-phenyl-benzamide;
3,4-Dimethoxy-N-naphthalen-2-ylmethyl-N-phenyl-benzamide;

N-(4-tert-Butyl-benzyl)-3,4-dimethoxy-N-phenyl-benzamide; or

N-Biphenyl-2-ylmethyl-3,4-dimethoxy-N-phenyl-benzamide.

In a more preferred embodiment of the compounds of Formula I, the present invention provides the compounds:

N-(3,4-Dichloro-benzyl)-N-(2-methoxy-phenyl)-benzamide;

N-(3,5-Di-tert-butyl-benzyl)-N-[4-(3-diethylamino-propyl)-phenyl]-benzamide;

N-(3,5-Bis-trifluoromethyl-benzyl)-N-[4-(3-diethylamino-propyl)-phenyl]-benzamide;

N-(3,5-Dibromo-benzyl)-N-[4-(3-diethylamino-propyl)-phenyl]-benzamide;

N-[4-(3-Diethylamino-propyl)-phenyl]-N-(4-methoxy-benzyl)-benzamide;

N-[4-(3-Diethylamino-propyl)-phenyl]-N-(3-methoxy-benzyl)-benzamide;

N-(3,4-Dichloro-benzyl)-N-[4-(3-diethylamino-propyl)-phenyl]-benzamide;

N-[4-(3-Diethylamino-propyl)-phenyl]-N-naphthalen-2-ylmethyl-benzamide;

N-Biphenyl-2-ylmethyl-N-[4-(3-diethylamino-propyl)-phenyl]-benzamide; or

3-Methyl-thiophene-2-carboxylic acid (4-iodo-phenyl)-(5,5,8,8-tetramethyl-5,6,7,8-tetrahydro-naphthalen-2-ylmethyl)-amide.

In a more preferred embodiment of the compounds of Formula I, the present invention provides the compounds:

N-(4-Methoxy-benzyl)-N-phenyl-benzamide;

N-(3-Methoxy-benzyl)-N-phenyl-benzamide;

3,4,5-Trimethoxy-N-naphthalen-2-ylmethyl-N-quinolin-3-yl-benzamide;

N-(4-tert-Butyl-benzyl)-3,4,5-trimethoxy-N-quinolin-3-yl-benzamide;

N-Biphenyl-2-ylmethyl-3,4,5-trimethoxy-N-quinolin-3-yl-benzamide;

3,4,5-Trimethoxy-N-(6-methoxy-pyridin-3-yl)-N-(5,5,8,8-tetramethyl-5,6,7,8-tetrahydro-naphthalen-2-ylmethyl)-benzamide;

N-(3,5-Di-tert-butyl-benzyl)-3,4,5-trimethoxy-N-(6-methoxy-pyridin-3-yl)-benzamide;

N-(3,4-Dichloro-benzyl)-3,4,5-trimethoxy-N-(6-methoxy-pyridin-3-yl)-benzamide;

4-Isopropyl-N-pyridin-3-yl-N-(5,5,8,8-tetramethyl-5,6,7,8-tetrahydro-naphthalen-2-ylmethyl)-benzamide; or 4-Isopropyl-N-(3-methoxy-benzyl)-N-pyridin-3-yl-benzamide.

In a more preferred embodiment of the compounds of Formula I, the present invention provides the compounds:

4-Isopropyl-N-naphthalen-2-ylmethyl-N-pyridin-3-yl-benzamide;

'N-(4-tert-Butyl-benzyl)-4-isopropyl-N-pyridin-3-yl-benzamide;

N-Biphenyl-2-ylmethyl-4-isopropyl-N-pyridin-3-yl-benzamide;

2-Ethoxy-N-pyridin-3-yl-N-(5,5,8,8-tetramethyl-5,6,7,8-tetrahydro-naphthalen-2-ylmethyl)-benzamide;

N-(3,5-Di-tert-butyl-benzyl)-2-ethoxy-N-pyridin-3-yl-benzamide;

N-(3,5-Dibromo-benzyl)-2-ethoxy-N-pyridin-3-yl-benzamide;

2-Ethoxy-N-(4-methoxy-benzyl)-N-pyridin-3-yl-benzamide;

2-Ethoxy-N-(3-methoxy-benzyl)-N-pyridin-3-yl-benzamide;

N-(3,4-Dichloro-benzyl)-2-ethoxy-N-pyridin-3-yl-benzamide; or

2-Ethoxy-N-naphthalen-2-ylmethyl-N-pyridin-3-yl-benzamide.

In a more preferred embodiment of the compounds of Formula I, the present invention provides the compounds:

N-(4-tert-Butyl-benzyl)-2-ethoxy-N-pyridin-3-yl-benzamide;

N-Biphenyl-2-ylmethyl-2-ethoxy-N-pyridin-3-yl-benzamide;

N-(6-Butoxy-pyridin-3-yl)-2-diethylamino-N-(5,5,8,8-tetramethyl-5,6,7,8-tetrahydro-naphthalen-2-ylmethyl)-acetamide;

N-(6-Butoxy-pyridin-3-yl)-N-(4-tert-butyl-benzyl)-2-diethylamino-acetamide;

'N-Biphenyl-2-ylmethyl-N-(6-butoxy-pyridin-3-yl)-2-diethylamino-acetamide;

N-(2-Methoxy-phenyl)-N-naphthalen-2-ylmethyl-benzamide;

N-(4-Methoxy-benzyl)-N-(2-methoxy-phenyl)-benzamide;

N-(3-Methoxy-benzyl)-N-(2-methoxy-phenyl)-benzamide;

N-Biphenyl-2-ylmethyl-N-(2-methoxy-phenyl)-benzamide; or

N-[4-(3-Diethylamino-propyl)-phenyl]-N-(5,5,8,8-tetramethyl-5,6,7,8-tetrahydro-naphthalen-2-ylmethyl)-benzamide.

In a more preferred embodiment of the compounds of Formula I, the present invention provides the compounds:

N-Biphenyl-2-ylmethyl-2-ethoxy-N-(6-methoxy-pyridin-3-yl)-benzamide;

N-Biphenyl-2-ylmethyl-2-methoxy-N-(6-methoxy-pyridin-3-yl)-benzamide;

N-Biphenyl-2-ylmethyl-2-methoxy-N-pyridin-3-ylmethyl-benzamide;

Benzo[b]thiophene-2-carboxylic acid biphenyl-2-ylmethyl-pyridin-4-yl-amide;

N-Biphenyl-2-ylmethyl-N-(6-methoxy-pyridin-3-yl)-2-nitro-benzamide;

N-Biphenyl-2-ylmethyl-4-ethoxy-N-(6-methoxy-pyridin-3-yl)-benzamide;

N-Biphenyl-2-ylmethyl-2-ethoxy-N-pyridin-3-ylmethyl-benzamide;

Benzo [1,3]dioxole-4-carboxylic acid biphenyl-2-ylmethyl-pyridin-3-ylmethyl-amide;

N-Biphenyl-2-ylmethyl-2-bromo-N-pyridin-3-ylmethyl-benzamide; or

3-Chloro-benzo [b]thiophene-2-carboxylic acid biphenyl-2-ylmethyl-pyridin-3-ylmethyl-amide.

In a more preferred embodiment of the compounds of Formula I, the present invention provides the compounds:

N-Biphenyl-2-ylmethyl-2-nitro-N-pyridin-3-ylmethyl-benzamide;

2-Benzyloxy-N-biphenyl-2-ylmethyl-N-pyridin-3-ylmethyl-benzamide;

N-Biphenyl-2-ylmethyl-4-ethoxy-N-pyridin-3-ylmethyl-benzamide;

N-Biphenyl-2-ylmethyl-4-methoxy-N-(4-methoxy-phenyl)-benzamide;

N-Biphenyl-2-ylmethyl-2-ethoxy-N-(4-methoxy-phenyl)-benzamide;

Benzo[1,3]dioxole-5-carboxylic acid biphenyl-2-ylmethyl-(4-methoxy-phenyl)-amide;

N-Biphenyl-2-ylmethyl-2,4-dimethoxy-N-(4-methoxy-phenyl)-benzamide;

2-Benzyloxy-N-biphenyl-2-ylmethyl-N-(4-methoxy-phenyl)-benzamide;

N-Biphenyl-2-ylmethyl-2-bromo-N-(4-methoxy-phenyl)-benzamide; or

Benzo[1,3]dioxole-4-carboxylic acid biphenyl-2-ylmethyl-(6-methoxy-pyridin-3-yl)-amide.

In a more preferred embodiment of the compounds of Formula I, the present invention provides the compounds:

N-Biphenyl-2-ylmethyl-2-ethoxy-N-pyridin-2-yl-benzamide;

N-Biphenyl-2-ylmethyl-2-bromo-N-pyridin-2-yl-benzamide;

N-Biphenyl-2-ylmethyl-2-nitro-N-pyridin-2-yl-benzamide;

2-Benzyloxy-N-biphenyl-2-ylmethyl-N-pyridin-2-yl-benzamide;

N-Biphenyl-2-ylmethyl-2-bromo-N-pyridin-3-yl-benzamide;

3-Chloro-benzo[b]thiophene-2-carboxylic acid biphenyl-2-ylmethyl-pyridin-3-yl-amide;

Benzo[b]thiophene-2-carboxylic acid biphenyl-2-ylmethyl-pyridin-3-yl-amide;

N-Biphenyl-2-ylmethyl-2-nitro-N-pyridin-3-yl-benzamide;

N-Biphenyl-2-ylmethyl-2-ethoxy-N-pyridin-4-yl-benzamide; or

N-Biphenyl-2-ylmethyl-2-methoxy-N-pyridin-4-yl-benzamide.

In a more preferred embodiment of the compounds of Formula I, the present invention provides the compounds:

Benzo[1,3]dioxole-4-carboxylic acid biphenyl-2-ylmethyl-pyridin-4-yl-amide;

N-Biphenyl-2-ylmethyl-2-bromo-N-pyridin-4-yl-benzamide;

N-Biphenyl-2-ylmethyl-2-nitro-N-pyridin-4-yl-benzamide;

2-Benzyloxy-N-biphenyl-2-ylmethyl-N-pyridin-4-yl-benzamide;

N-Biphenyl-2-ylmethyl-4-ethoxy-N-pyridin-4-yl-benzamide;

Benzo[b]thiophene-2-carboxylic acid biphenyl-2-ylmethyl-pyridin-3-ylmethyl-amide;

N-Biphenyl-2-ylmethyl-N-(4-methoxy-phenyl)-2-methylsulfanyl-benzamide;

N-Biphenyl-2-ylmethyl-2-isopropylsulfanyl-N-(4-methoxy-phenyl)-benzamide;

N-Biphenyl-2-ylmethyl-N-(3-methoxy-phenyl)-2-propylsulfanyl-benzamide; or

N-Biphenyl-2-ylmethyl-N-(3-methoxy-phenyl)-2-methylsulfanyl-benzamide.

In a more preferred embodiment of the compounds of Formula I, the present invention provides the compounds:

N-Biphenyl-2-ylmethyl-2-isopropylsulfanyl-N-(3-methoxy-phenyl)-benzamide;

2-Benzylsulfanyl-N-biphenyl-2-ylmethyl-N-(3-methoxy-phenyl)-benzamide;

2-Benzylsulfanyl-N-biphenyl-2-ylmethyl-N-(4-chloro-phenyl)-benzamide;

N-Biphenyl-2-ylmethyl-N-(3,4-dimethoxy-phenyl)-2-propylsulfanyl-benzamide;

N-Biphenyl-2-ylmethyl-N-(3,4-dimethoxy-phenyl)-2-methylsulfanyl-benzamide;

N-Biphenyl-2-ylmethyl-N-(3,4-dimethoxy-phenyl)-2-isopropylsulfanyl-benzamide;

N-Biphenyl-2-ylmethyl-N-(3,4-dimethoxy-phenyl)-3-phenylsulfanyl-benzamide;

2-Benzylsulfanyl-N-biphenyl-2-ylmethyl-N-(3,4-dimethoxy-phenyl)-benzamide;

'N-Biphenyl-2-ylmethyl-N-(4-methoxy-phenyl)-2-(propane-1-sulfinyl)-benzamide; or 'N-Biphenyl-2-ylmethyl-N-(4-methoxy-phenyl)-2-(propane-2-sulfinyl)-benzamide.

In a more preferred embodiment of the compounds of Formula I, the present invention provides the compounds:

'2-Benzenesulfinyl-N-biphenyl-2-ylmethyl-N-(4-chloro-phenyl)-benzamide;

'N-Biphenyl-2-ylmethyl-N-(3,4-dimethoxy-phenyl)-2-(propane-1-sulfinyl)-benzamide;

N-Biphenyl-2-ylmethyl-N-(3,4-dimethoxy-phenyl)-2-(propane-2-sulfinyl)-benzamide; or N-Biphenyl-2-ylmethyl-N-(3,4-dimethoxy-phenyl)-2-phenylmethanesulfinyl-.

Also provided is a pharmaceutical composition comprising a compound of Formula I.

Also provided is a method of treating atherosclerosis, the method comprising administering to a patient having or at risk of having atherosclerosis a therapeutically effective amount of a compound of Formula I.

Also provided is a method of treating restenosis, the method comprising administering to a patient having or at risk of having restenosis a therapeutically effective amount of a compound of Formula I.

Also provided is a method of treating coronary heart disease, the method comprising administering to a patient having or at risk of having coronary heart disease a therapeutically effective amount of a compound of Formula I.

Also provided is a method of treating hyperlipidemia, the method comprising administering to a patient having hyperlipidemia, a therapeutically effective amount of a compound of Formula I.

Also provided is a method of treating hyperlipoproteinemia, the method comprising administering to a patient having hyperlipoproteinemia a therapeutically effective amount of a compound of Formula I.

Also provided is a method of treating hypercholesterolemia, the method of comprising administering to a patient having hyperchloesterolemia a therapeutically effective amount of a compound of Formula I.

Also provided is a method of treating hypertriglyceridemia, the method comprising administering to a patient having hypertriglyceridemia a therapeutically effective amount of a compound of Formula I.

Also provided is a method of treating obesity, the method of comprising administering to an obese patient a therapeutically effective amount of a compound of Formula I.

Also provided is a method of lowering plasma concentrations of apoB containing lipoproteins, the method comprising administering to a patient in need of lowering of apoB containing lipoproteins in plasma a therapeutically effective amount of a compound of Formula I.

Also provided is a method of lowering the plasma concentration of Lp(a) the method comprising administering to a patient in need of Lp(a) lowering a therapeutically effective amount of a compound of Formula I.

Also provided is a method of lowering the plasma concentration of LDL, the method comprising administering to a patient in need of LDL lowering a therapeutically effective amount of a compound of Formula I.

Also provided is a method of lowering the plasma concentration of triglycerides, the method comprising administering to a patient in need of triglyceride lowering a therapeutically effective amount of a compound of Formula I.

DETAILED DESCRIPTION OF THE INVENTION

The term "alkyl" means a straight or branched hydrocarbon and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl. Preferred alkyl groups have from 1 to 6 carbon atoms ($C_1$–$C_6$ alkyl).

The term "aryl" means an aromatic ring such as phenyl, 5-fluorenyl, 1-naphthyl, or 2-naphthyl, unsubstituted or substituted by 1 to 3 substituents selected from —$C_1$–$C_6$ alkyl, —$OC_1$–$C_6$ alkyl and —$SC_1$–$C_6$ alkyl, —OH, —SH, —F, —CN, —Cl, —Br, —I, —$CF_3$, —$OCF_3$, —$NO_2$, —$CO_2$H, —$CO_2C_1$–$C_6$ alkyl,

—$NH_2$, —$NHC_1$–$C_6$ alkyl, or —$N(C_1$–$C_6$alkyl$)_2$.

The term "pyridyl" means a radical given by the following formula:

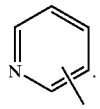

The line crossing the double bond indicates that the pyridyl group be attached by any carbon atom in the ring which is available. Preferably, the pryidyl group is a 2-pyridyl group.

The term "substituted pyridyl" means a pyridyl wherein one to four substitutionally available positions are replaced by substituents selected from —$C_1$–$C_6$ alkyl, —$OC_1$–$C_6$ alkyl, —$SC_1$–$C_6$ alkyl, halogen, nitro, cyano —OH, —SH, —F, —$CF_3$, —$OCF_3$, —$NO_2$, —$CO_2$H, —$CO_2C_1$–$C_6$ alkyl, —$NH_2$,

—$CONR^8R^9$, —$SO_2$alkyl, —$SO_2NH_2$, —$NHC_1$–$C_6$ alkyl, or —$N(C_1$–$C_6$alkyl$)_2$. More preferably, the substituted pyridyl will have one to two substituents.

The term "substituted phenyl" means a phenyl wherein one to five substitutionally available positions are replaced by substituents selected from —$C_1$–$C_6$ alkyl, —$OC_1$–$C_6$ alkyl, —$SC_1$–$C_6$ alkyl, halogen, nitro, cyano —OH, —SH, —F, —$CF_3$, —$OCF_3$, —$NO_2$, —$CO_2$H, —$CO_2C_1$–$C_6$ alkyl, —$NH_2$,

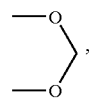

—$CONR^8R^9$, —$SO_2$alkyl, —$SO_2NH_2$, —$NHC_1$–$C_6$ alkyl, or —$N(C_1$–$C_6$alkyl$)_2$. More preferably, the substituted phenyl will have one to two substituents.

The term "heteroaryl" means an aromatic ring containing one or more heteroatoms. Examples of heteroaryl radicals include thienyl, furyl, pyrrolyl, thiazoyl, pyridyl, imidazolyl, or indolyl, substituted or unsubstituted by 1 or 2 substituents from the group of substituents described above for aryl. Examples of heteroatoms include nitrogen, oxygen, sulfur, and phosphorus.

The term "cycloalkyl" means a saturated hydrocarbon ring, and includes for example, cyclopropyl, cyclobutyl, cyclopentyl, cyclohexyl, adamantyl, and the like. The cycloalkyl group can be substituted with from 1 to 3 substituents from the group of substituents described above for aryl.

The symbol "—" means a bond.

The term "patient" means all animals including humans. Examples of patients include humans, cows, dogs, cats, goats, sheep, pigs, rabbits, and rats.

A "therapeutically effective amount" is an amount of a compound of the present invention that when administered to a patient ameliorates a symptom of atherosclerosis, obesity, coronary heart disease, restenosis hyperlipoproteinemia, hypercholesterolemia, hypertriglyceridemia, or lowers plasma levels of Lp(a), LDL, triglycerides VLDL, IDL chylomicrons or HDL. A therapeutically effective amount of a compound of the present invention can be easily determined by one skilled in the art by administering a quantity of a compound to a patient and observing the result. In addition, those skilled in the art are familiar with identifying patients having restenosis, coronary heart disease, atherosclerosis or who are at risk of having restenosis, coronary heart disease, atherosclerosis. Moreover, those skilled in the art are familiar with identifying patients having hyperlipoproteinemia, hypercholesterolemia, hypertriglyceridemia, or who are obese.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. However, the specific dosage used can vary. For example, the dosage can depended on a numbers of factors including the requirements of the patient, the severity of the condition being treated, and the pharmacological activity of the compound being used. The determination of optimum dosages for a particular patient is well-known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The exemplified compounds of the present invention were synthesized using multiple parallel synthesis (combinatorial chemistry), but can also be prepared using standard laboratory scale organic reactions. It is also contemplated that compounds of the present invention may also be prepared through metabolism. It is intended that the scope of the application include compounds synthesized by any method known to those skilled in the art.

The examples presented below are intended to illustrate particular embodiments of the invention, and are not intended to limit the scope of the specification or the claims in any way.

Procedure 1

For Multiple, Simultaneous Solution Phase Synthesis
Combinatorial Chemistry

A blend of powdered bases was prepared as follows:

Sodium hydroxide pellets (3.2 g), anhydrous potassium carbonate (2.8 g) and tetrabutylammonium hydrogen sulfate (0.28 g) were ground together to give a uniform powder. The powder was stored under argon.

With regard to Table 1, a solution of reagent 2 (0.11 mmol) in toluene (1 mL) was added to reagent 1 (0.1 mmol) in a 2-dram glass vial. A blend of powered bases (described above) (0.04 g) was then added with a teflon-backed cap, and the reaction mixture was heated at 80° C. and shaken on an orbital shaker for 2.5 hours. To the reaction mixture was added tris(2-aminioethyl)amine, polymer bound [Calbiochem-Novabiochem, San Diego, Calif.] (0.06 g). After 45 minutes at 80° C., the reaction mixture was cooled to room temperature and shaken overnight. Dioxane (1.5 mL) added and silica gel (0.1 g) was added. The solids were removed by filtration and washed with dioxane (1.5 mL). The filtrate, collected in a tarred 2-dram vial, was concentrated to dryness. Further purification was achieved by partitioning between ethyl acetate and water. The organic phase was concentrated to dryness to yield the desired product.

The product was analyzed by liquid chromatography-mass spectrometry (LCMS). Conditions used for analytical work were an Alltech (Deerfield, Ill.), Alltima (Deerfield, Ill.), C18 column (150 mm ID, 4.6 mm length). The mobile phase (acetonitrile/water/0.05% trifluoroacetic acid at a flow of 1 mL/min) was used as a linear gradient of 50%–95% acetonitrile over 4 minutes then 95% acetonitrile over 9 minutes. Detection was at 214 nm. The compounds described in Table 1 were prepared simultaneously. The starting materials, called Reagents 1 and Reagents 2, are different for each individual compound synthesized and are described in Table 1. Reagents 1 and Reagents 2 are commercially available unless otherwise noted.

In general, the reagents can be obtained from Aldrich Chemical Company, Milwaukee, Wis.; Lancaster Synthesis Ltd., Lancaster, UK; or Fluka, Bucha, Switzerland.

Procedure 2

For Multiple, Simultaneous Solution Phase Synthesis.

With regard to Table 2, a solution of Reagent 3 (0.05 mmol) and a solution of pyridine (50 mmol) in dichloroethane (0.3 mL) were sequentially added to a glass 2-dram vial. A solution of Reagent 4 (0.1 mmol) in dichloroethane (0.5 mL) was added. The vial was sealed with a teflon-backed cap, and the reaction mixture was shaken on an orbital shaker for 4 days. Tris(2-aminioethyl)amine, polymer bound [Calbiochem-Novabiochem] (0.120 g) was added. After 2 hours the solids were removed by filtration washed with dichloromethane (2×2 mL). The filtrate, collected in a tarred 2-dram vial, was concentrated to dryness.

Conditions used for analytical work were an Alltech, Alltima, C18 column (150 mm ID, 4.6 mm length). The mobile phase (acetonitrile/water/0.05% trifluoroacetic acid at a flow of 1 mL/minute) was used as a linear gradient of 50%–95% acetonitrile over 6 minutes, then 95% acetonitrile over 4 minutes, detection was at 214 nm. Conditions B used for analytical work were an Alltech, Alltima, C18 column (150 mm ID, 4.6 mm length). The mobile phase (acetonitrile/water/0.05% trifluoroacetic acid at a flow of 1 mL/minute) was used as a linear gradient of 50%–98% acetonitrile over 6.50 minutes, then 95% acetonitrile over 3.1 minutes, detection was at 214 nm.

The compounds described in Table 2 were prepared simultaneously. Reagents 3 and Reagents 4 are different for each individual compound and are described in Table 2. Reagents 3 are prepared as described herein. Reagents 4 are commercially available or prepared from the commercially available acid using oxalyl chloride and a catalytic amount of dimethylformamide (DMF) in dichloromethane unless otherwise noted.

Procedure 3

For Multiple, Simultaneous Solution Phase Synthesis

A solution of Reagent 3 (0.05 mm) and a solution of pyridine (5 mm) in dichloroethane (0.3 mL) were sequentially added by Tecan liquid handling robot to a glass 2 dram vial. A solution of Reagent 4 (0.1 mm) in dichloroethane (0.5 mL) was added by Tecan liquid handling robot. The vial was sealed with a teflon-backed cap, and the reaction mixture was shaken on an ISS orbital shaker for 4 days. Tris(2-aminioethyl)amine, polymer bound [Calbiochem-Novabiochem] (0.120 g) was added. After 2 hours the solids were removed by filtration through a Specdisk filter using a Tecan liquid handling robot to transfer the sample and washed with dichloromethane (2×2 mL). The filtrate, collected in a tarred 2-dram vial, was concentrated to dryness by evaporation. The product was analyzed by LCMS. Conditions used for analytical work were an Alltech, Alltima, C18 column (150 mm ID, 4.6 mm length). The mobile phase (acetonitrile/water/0.05% trifluoroacetic acid at a flow of 1 mL/min) was used as a linear gradient of 50%–95% acetonitrile over 6 minutes, then 95% acetonitrile over 4 minutes, detection was at 214 nm.

Further purification was achieved by reverse phase high-pressure liquid chromatography. Conditions used for preparative work were an Alltech, Alltima, C18 column (22 mm ID), 150 mm length). The mobile phase (acetonitrile/water/ 0.05% trifluoroacetic acid at a flow of 23 mL/min) was used as a linear gradient of 50%–98% acetonitrile over 12 minutes, detection was at 214 nm. Concentration of the appropriate fraction gave the title compound. Analysis of the product was by MS.

The compounds described in Table 3 were prepared simultaneously. Reagents 5 and Reagents 6 are different for each individual compound and are described in Table 3. Reagents 5 are prepared as described herein. Reagents 6 are commercially available or prepared from the commercially available acid using oxalyl chloride and a catalytic amount of DMF in dichloromethane unless otherwise noted.

Procedure 4

For Multiple, Simultaneous Solution Phase Synthesis

A solution of Reagent 7 (0.05 mm) and a solution of pyridine (5 mm) in dichloroethane (0.3 mL) were sequentially added to a glass 2-dram vial. A solution of Reagent 8 (0.1 mm) in dichloroethane (0.5 mL) was added. The vial was sealed with a teflon-backed cap, and the reaction mixture was shaken on an orbital shaker for 4 days. Tris(2-aminioethyl)amine, polymer bound [Calbiochem-Novabiochem, San Diego, Calif.] (0.120 g) was added. After 2 hours the solids were removed by filtration and washed with dichloromethane (2×2 mL). The filtrate, collected in a tarred 2-dram vial, was concentrated to dryness by evaporation. An amount of the product (0.03 mmol) was removed from each sample to be used in Procedure 5.

The product was analyzed by LCMS. Conditions used for analytical work were an Alltech, Alltima, C18 column (150 mm ID, 4.6 mm length). The mobile phase (acetonitrile/ water/0.05% trifluoroacetic acid at a flow of 1 mL/min) was used as a linear gradient of 50%–98% acetonitrile over 5 minutes. Then 98% acetonitrile over 5 minutes, detection was at 214 nm. Further purification was achieved by reverse phase high-pressure liquid chromatography. Conditions used for preparative work were an Alltech, Alltima, C18 column (22 mm ID, 150 mm length). The mobile phase (acetonitrile/water/0.05% trifluoroacetic acid at a flow of 23 mL/min) was used as a linear gradient of 50%–98% acetonitrile over 12 minutes, detection was at 214 nm. Concentration of the appropriate fraction gave the title compound. Analysis of the product was by MS. The compounds described in Table 3 were prepared simultaneously. Reagents 7 and Reagents 8 are different for each individual compound and are described in Table 4. Reagents 7 are prepared as described herein. Reagents 8 are commercially available or prepared from a commercially available acid using oxalyl chloride and a catalytic amount of DMF.

Procedure 5

For Multiple, Simultaneous Solution Phase Synthesis

A solution of Reagent 9 (the unpurified products from Procedure 4) (0.03 mm) was split into a 2-dram glass vial. Tetrahydrofuran/water/methanol (2:1:1) (1 mL) was added together with sodium periodate (0.15 mm). The reaction mixture was stirred at room temperature overnight. The organic components were removed by evaporation and the aqueous phase extracted by ethyl acetate. The filtrate, collected in a tarred 2-dram vial, was concentrated to dryness by evaporation. The product was analyzed by LCMS. Conditions used for analytical work were an Alltech, Alltima, C18 column (150 mm ID, 4.6 mm length). The mobile phase (acetonitrile/water/0.05% trifluoroacetic acid at a flow of 1 ML/min) was used as a linear gradient of 50%–98% acetonitrile over 7.50 minutes then 98% acetonitrile over 2.10 minutes, detection was at 214 nm. Further purification was achieved by reverse phase high-pressure liquid chromatography. Conditions used for preparative work were an Alltech, Alltima, C18 column (22 mm ID, 150 mm length). The mobile phase (acetonitrile/water/0.05% trifluoroacetic acid at a flow of 23 mL/min) was used as a linear gradient of 50%–98% acetonitrile over 12 minutes, detection was at 214 nm. Concentration of the appropriate fraction gave the compounds listed in Table 5. Analysis of the product was by MS. The compounds described in Table 5 were prepared simultaneously.

Starting Materials for Combinatorial Chemistry

EXAMPLE 1

2-Methylenedioxybenzoic Acid

Freshly prepared Jones reagent (0.2 mmol) was added dropwise (until a brown color persisted in the reaction) to a solution of 2-methylenedioxybenzaldehyde (1.0 g, 6.67 mmol) in 10 mL of acetone at 0° C. The reaction was completed after 4 hours at 0° C., and it was poured onto ethyl ether (20 mL). The ether solution was then washed with brine and extracted with 1N NaOH solution. The NaOH extract was acidified with concentration HCl, and product was extracted out with ether (3×10 mL). Ether layers were combined, dried, and evaporated to give 0.6 g pure product; this compound was used for the next step without further purification (54%). M+167.0

EXAMPLE 2

N,N-2-pyridyl,2-phenylbenzylamine

Lithium aluminum hydride (LAH) (0.291 g, 7.6 mmol) was added in portions to a solution of N-2-pyridinyl-2-biphenylamide (1.52 g, 5.5 mmol) in tetrahydrofuran (THF) (50 mL) at room temperature. The reaction was completed after 5 hours at room temperature and was quenched by the sequential addition of 0.29 mL water, 0.29 mL 2N NaOH, and then 0.58 mL water. The solution was then filtered, and the solvent was evaporated. The residue was redissolved in ethyl acetate, which was washed with brine. The ethyl acetate layer was dried and evaporated to give 0.7 g pure product (48%). M+261.1

EXAMPLE 3

N,N-4-pyridyl,2-phenylbenzylamine

This compound was prepared by the same procedure as in Example 2, except N-4-pyridinyl-2-biphenylamide was used instead of N-2-pyridinyl-2-biphenylamide. M+261.1

EXAMPLE 4

N,N-3-pyridyl,2-phenylbenzylamine

This compound was prepared by the same procedure as in Example 2, except N-3-pyridinyl-2-biphenylamide was used instead of N-2-pyridinyl-2-biphenylamide. M+261.1

EXAMPLE 5

N,N-3-(5-methoxypyridyl),2-phenylbenzylamine

This compound was prepared by the same procedure as in Example 2, except N-2-(5-methoxypyridinyl)-2-biphenylamide was used instead of N-2-pyridinyl-2-biphenylamide. The purified product was an oil. M+291.1

EXAMPLE 6
N,N-3-methylpyridyl,2-phenylbenzylamine

PBr$_3$ (1 mL, 10.6 mmol) in ether (25 mL) was added dropwise to a solution of 2-biphenylmethanol (4 g, 21.7 mmol) in ether (50 mL). The reaction was stirred at room temperature for 1 hour. 100% Ethanol was added, and the reaction was stirred for half an hour at room temperature. The solvent was evaporated, and the residue was redissolved in ethyl acetate. The ethyl acetate layer was washed sequentially with saturated Na$_2$CO$_3$, brine, and dried. The solvent was evaporated, and the product 2-biphenylbromomethane (5.4 g, 21.7 mmol) was dissolved in isopropanol. 3-Aminomethylpyridine (2.2 mL, 21.7 mmol) and K$_2$CO$_3$ (4.46 g, 32.3 mmol) were added, and the mixture was refluxed for 1 hour. The solvent was evaporated. The residue was redissolved in ethyl acetate, which was sequentially washed with saturated Na$_2$CO$_3$ and brine. The ethyl acetate layer was dried, and evaporated to give 1.8 g pure product (30%). M+275.1

EXAMPLE 7
Biphenyl-2-ylmethyl-(3-methoxy-phenyl)-amine

A solution of borane-dimethylsulfide complex (2.0 M, 9 mL, 18 mmol) was added to a solution of biphenyl-2-carboxylic acid (3-methoxy-phenyl)-amide (3.03 g 10 mmol) in toluene (10 mL). The reaction mixture was refluxed and stirred for 42 hours. The reaction mixture was cooled to room temperature, 10% aqueous potassium carbonate (10 mL) was added, and the reaction mixture was vigorously stirred for 30 minutes. Extraction of the aqueous layer with ethyl acetate followed by concentration gave the crude product. Purification by silica gel column chromatography using 20% ethyl acetate in hexanes as the eluant afforded the pure product (1.4 g). MH+290: $^1$H (CDCl$_3$) δ 3.72 (3H, s), 4.23 (2H, s), 6.07 (1H, m), 6.14 (1H, dm, J=8), 6.25 (1H, dm, J=8), 7.03 (1H, t, J=8), 7.22–7.32 (8H, m), 7.52 (1H, m).

EXAMPLE 8
Biphenyl-2-ylmethyl-(4-methoxy-phenyl)-amine

This compound was prepared by the same procedure as in Example 7, except biphenyl-2-carboxylic acid (4-methoxy-phenyl)-amide was used instead of biphenyl-2-carboxylic acid (3-methoxy-phenyl)-amide. MH+290: $^1$H (CDCl$_3$) δ 3.73 (3H, s), 4.22 (2H, s), 6.50 (2H, d, J=9), 6.70 (2H, d, J=9), 7.25–732 (8H, m), 7.41 (1H, m).

EXAMPLE 9
Biphenyl-2-ylmethyl-(4-chloro-phenyl)-amine

This compound was prepared by the same procedure as in Example 7, except biphenyl-2-carboxylic acid (4-chloro-phenyl)-amide was used instead of biphenyl-2-carboxylic acid (3-methoxy-phenyl)-amide. MH+296, 294: $^1$H (CDCl$_3$) δ 4.18 (2H, s), 6.40 (2H, d, J=10), 7.01 (2H, d, J=9), 7.20–7.43 (9H, m).

EXAMPLE 10
Biphenyl-2-ylmethyl-(3,4-dimethoxy-phenyl)-amine

Potassium carbonate (1.38 g, 10 mmol), catalytic amount of potassium iodide, and 3,4-dimethoxyaniline (1.53 g 10 mmol) were added to a solution of 2-(bromomethyl) biphenyl (1.83 mL, 10 mmol) in acetonitrile (200 mL). The reaction mixture was heated and stirred at 80° C. for 18 hours, then was cooled to room temperature. The solid was filtered and the filtrate concentrated to dryness. Purification by silica gel column chromatography using 20% ethyl acetate in hexanes as the eluant afforded the pure product (1.04 g). MH+320: $^1$H (CDCl$_3$) δ 3.77 (3H, s), 3.78 (3H, s), 4.21 (2H, s), 6.05 (1H, dd, J=8, 3), 6.14 (1H, m) 6.67 (1H, d, J=8), 7.28–7.42 (8H, m), 7.54 (1H, m).

EXAMPLE 11
Biphenyl-2-carboxylic acid (3-methoxy-phenyl)-amide

Pyridine (3.6 mL, 45 mmol) and 3-methoxyaniline (1.54 g, 12.5 mmol) were added to a solution of 2-phenylbenzoyl chloride (3.25 g, 15 mmol) in dichloromethane (30 mL) The reaction mixture was stirred at room temperature for 2.5 hours. 1M HCl solution (45 mL) was added, and the organic layer was washed with 1M NaOH solution (10 mL), aqueous sodium bicarbonate (30 mL), and brine (30 mL). The organic phase was concentrated to dryness to give the title compound as a tan solid (3.92 g). MH+304: $^1$H (D$_6$-DMSO) δ 3.67 (3H, s), 6.60 (1H, dd, J=8, 2), 7.04 (1H, d, J=8), 7.14 (1H, t, J=8), 7.18 (1H, m), 7.23–7.57 (9H, m), 10.0 (1H, s, NH).

EXAMPLE 12
Biphenyl-2-carboxylic acid (4-chloro-phenyl)-amide

This compound was prepared by the same procedure as in Example 11, except 4-chloroaniline (1.6 g, 12.5 mmol) was used instead of 3-methoxyaniline. MH+310, 308: $^1$H (D$_6$-DMSO) δ 7.20–7.60 (13H, m).

EXAMPLE 13
Biphenyl-2-carboxylic acid (4-methoxy-phenyl)-amide

This compound was prepared by the same procedure as in Example 11, except 4-methoxyaniline was used instead of 3-methoxyaniline. MH+304: $^1$H (D$_6$-DMSO) δ 3.68 (3H, s), 6.81 (2H, d, J=7), 7.22–7.56 (11H, m), 10.0 (1H, s, NH).

EXAMPLE 14
2-Benzoyl-N-biphenyl-2-ylmethyl-N-pyridin-3-ylmethyl-benzamide

Polymer-supported morpholine [Aldrich, Milwaukee, Wis.] (0.15 g), N,N-3-methylpyridyl,2-phenylbenzylamine (0.05 g, 0.18 mmol), and 2-benzoylbenzoyl chloride (0.066 g, 0.27 mmol) were mixed in dichloromethane (2 mL), and the reaction was shaken at room temperature using an orbital shaker. After 4.5 hours, 2-benzoylbenzoyl chloride (0.022 g, 0.27 mmol) was added. After another 18 hours, Tris(2-aminioethyl)amine, polymer bound [Novabiochem] (0.250 g) was added. After an additional 2 hours, the reaction mixture was filtered. The filtrate concentrated to dryness to yield the title compound (0.078 g). MH+483: HPLC data RT=6.77 minutes. Conditions used for analytical work were an Alltech, Alltima, C18 column (150 mm ID, 4.6 mm length). The mobile phase (acetonitrile/water/0.1% trifluoroacetic acid at a flow of 1 mL/min) was used as a linear gradient of 40%–100% acetonitrile over 10 minutes, then 100% acetonitrile over 5 minutes, detection was at 214 nm.

EXAMPLE 15
Naphthalene-2-carboxylic acid (4-iodo-phenyl)-amide

A suspension of 2-napthoic acid (6.97 g, 40.5 mmol) and thionyl chloride (50 mL) was refluxed for 3 hours to form the acid chloride. The excess thionyl chloride was evaporated. 4-Iodoaniline (9.05 g, 40.5 mmol) and triethylamine (5.7 mL) were added to the solution of the acid chloride in dichloromethane (100 mL). Water (75 mL) was added after 1 hour, and the mixture was filtered. The filtrate was washed with water and ethanol. The product was recrystallized from toluene-ethanol (95%). M+373.3, mp 254–256° C.

EXAMPLE 16
4-Methyl-3-(3-nitro-benzoylamino)-benzoic acid methyl ester

Ethyl-4-nitrobenzoate was reduced with hydrogen/Pd(C) in methanol. The solvent was evaporated, and ethyl-4-aminobenzoate was recrystallized from ethyl acetate/hexane.

The title compound was synthesized by the same procedure as for Example 15 except 3-nitrobenzoic acid and ethyl-4-aminobenzoate were used instead of 2-napthoic acid and 4-iodoaniline. M+315.3, mp 208–209° C.

EXAMPLE 17
2-Benzyl-N-(4-methoxy-phenyl)-benzamide.
Procedure: Ukr. Khim. Zh. (Russ. Ed.) (1984), 50(1), 71–5.

EXAMPLE 18
2-Benzylsulfanyl-N-(4-methoxy-phenyl)-benzamide
Triethyl amine (16.4 g, 162 mmol) and benzoyl chloride (12.3 g, 97.3 mmol) were added to a solution of 2-mercaptobenzoic acid (10 g, 64.8 mmol) in dioxane (150 mL). The reaction was stirred overnight. 1N HCl (300 ML) was added followed by the addition of water (200 mL). The solution was filtered and the product was washed with water and then pentane giving the product, 2-benzylsulfanyl-benzoic acid.
The title compound was synthesized by the same procedure as for Example 15, except 2-benzylsulfanyl-benzoic acid and 4-methoxyaniline were used instead of 2-napthoic acid and 4-iodoaniline. M+364.2

EXAMPLE 19
3,4-Dimethoxy-N-phenyl-benzamide
Procedure: *Tetrahedron Lett.* (1996), 37(18), 3169–3170.

EXAMPLE 20
N-(2-Methoxyphenyl)-benzamide
Procedure: *J. Chem. Soc., Chem. Commun.* (1989), (19), 1450–1.

EXAMPLE 21
N-{4-[3-(Diethylamino)propyl]phenyl}-benzamide
p-Nitroacetophenone (33.0 g, 200 mmol), diethyl amine HCl (28.5 g, 260 mmol), and paraformaldehylde (8.1 g, 90 mmol) were mixed with conc. HCl (0.4 mL) and 95% ethanol (32 mL). The solution was refluxed for 2 hours. The solution was cooled and acetone (160 mL) was added. 3-(diethylamino)-4'-nitro-propiophenone was collected by filtration. M+311.4, mp 110–111° C.
A slurry of 5% Pd/C (2.5 g) in glacial acetic acid (30 mL) was added to a solution of 3-(diethylamino)-4'-nitro-propiophenone (14.33 g, 50 mmol) in glacial acetic acid (150 mL). The mixture was shaken on a Parr shaker under hydrogen pressure for about 20 hours. The catalyst was filtered, and the solvent was evaporated to dryness. The resulting amber liquid was dissolved in ether and washed twice with 2N NaOH (150 mL). The ether layer was dried and evaporated to give N,N-diethyl-3-(p-nitrophenyl)-propylamine as an oil.
Benzoylchloride (6.33 g, 45 mmol) in pyridine (50 mL) was added over a 15-minute period to a solution of N,N-diethyl-3-(p-nitrophenyl)-propylamine (9.4 g, 45 mmol) in pyridine (50 mL). The solution was refluxed for 1.5 hours. The solvent was evaporated, giving a brown oil. The oil was dissolved in dichloromethane (300 mL) and washed with 1N NaOH (200 mL). The dichloromethane layer was dried and evaporated. Toluene (100 mL) was added to the resulting oil and re-evaporated. The semi-solid residue was washed with pentane, then recrystalized from cyclohexane (125 mL) to give the title compound.

EXAMPLE 22
Benzoic acid, 2-[(2-pyridinylcarbonyl)amino]-, methyl ester
Procedure: Japanese Patent No. 55031099.

EXAMPLE 23
3-Methyl-thiophene-2-carboxylic acid (4-iodo-phenyl)-amide
This compound was synthesized by the same procedure as for Example 15, except 3-methyl-2-thiophenecarboxylic acid and 4-iodoaniline were used instead of 2-napthoic acid and 4-iodoaniline. M+1=344.2, mp 141~142° C.

EXAMPLE 24
3,4,5-Trimethoxy-N-quinolin-3-yl-benzamide
Procedure: WO 97/48694.

EXAMPLE 25
3,4,5-Trimethoxy-N-(6-methoxy-pyridin-3-yl)-benzamide
This compound was synthesized by the same procedure as for Example 15, except 3,4,5-trimethoxybenzoic acid and 5-amino-2-methoxypyridine were used instead of 2-napthoic acid and 4-iodoaniline. Tiny off-white needles. M+319.3

EXAMPLE 26
p-Isopropyl-N-3-pyridyl-benzamide
This compound was synthesized by the same procedure as for Example 15 except cuminic acid and 3-aminopyridine were used instead of 2-napthoic acid and 4-iodoaniline. White needles. M+241.3

EXAMPLE 27
2-Ethoxy-N-pyridin-3-yl-benzamide
Procedure: *J. Chromatogr.* (1979), 171, 462–5.

EXAMPLE 28
N-(6-Butoxy-pyridin-3-yl)-2-diethylamino-acetamide
Procedure: Aldrich Chemical Company, Milwaukee, Wis.

EXAMPLE 29
α-Phenyl-N-4-pyridinyl-Benzeneacetamide
Procedure: U.S. Pat. No. 4,180,670.

EXAMPLE 30
2-Oxo-N-3-pyridinyl-1-pyrrolidineacetamide
Procedure: *Collect. Czech. Chem. Commun.* (1990), 55(11), 2756–64.

EXAMPLE 31
2,2-Dimethyl-N-pyridin-3-yl-propionamide
Procedure: *J. Chem. Soc.*, Perkin Trans. 1 (1989), (3), 639–42.

EXAMPLE 32
4-Pyridinyl-benzamide
Procedure: *Proc. Arkansas Acad. Sci.* (1993), 47, 107–9.

EXAMPLE 33
N-(4-Iodo-phenyl)-isonicotinamide
This compound was synthesized by the same procedure as for Example 15, except isonicotinic acid and 4-iodoaniline were used instead of 2-napthoic acid and 4-iodoaniline. M+325.1, mp 245–250° C.

EXAMPLE 34
2-(Propylthio)-benzoic acid
Procedure: *Tet.* (1974), 30(16), 2641.

EXAMPLE 35
2-Methylsulfanyl-benzoic acid
Procedure: *Tet.* (1974), 30(16), 2641.

EXAMPLE 36
2-[(1-Methylethyl)thio]-benzoic acid
Procedure: *Tet.* (1974), 30(16), 2641.

EXAMPLE 37

3-(Phenylthio)-benzoic acid
  Procedure: U.S. Pat. No. 4,124,370.

EXAMPLE 38

2-[(4–Chlorophenyl)thio]-benzoic acid
  Procedure: *Tet.* (1992), 48(36), 7747.

EXAMPLE 39

2-Benzylsulfanyl-benzoic acid

Procedure: *Chem. Ind.* (London) (1973), No. 6, 277.

The patents and literature documents cited herein are hereby incorporated by reference.

TABLE 1

| Example No. | Name of Product | Reagent 1 | Reagent 2 | LCMS | LCMS RT, Minutes |
|---|---|---|---|---|---|
| 40 | 2-Benzylsulfanyl-N-(4-methoxy-benzyl)-N-(4-methoxy-phenyl)-benzamide | 2-Benzylsulfanyl-N-(4-methoxy-phenyl)-benzamide | 4-methoxybenzyl chloride | MH + 470.2 | 5.67 |
| 41 | N-(3,5-Di-tert-butyl-benzyl)-3,4-dimethoxy-N-phenyl-benzamide | 3,4-dimethoxy-N-phenyl-benzamide | 3,5-bis(tert-butyl) benzyl bromide (?? NEEDS A PROCEDURE) | MH + 460.3 | 7.31 |
| 42 | N-(3,5-Bis-trifluoromethyl-benzyl)-3,4-dimethoxy-N-phenyl-benzamide | 3,4-dimethoxy-N-phenyl-benzamide | 3,5-bis (trifluouromethyl) benzyl bromide | MH + 484.2 | 5.67 |
| 43 | N-(3,5-Dibromo-benzyl)-3,4-dimethoxy-N-phenyl-benzamide | 3,4-dimethoxy-N-phenyl-benzamide | 3,5-dibromobenzyl bromide | MH + 508.0, 506.0, 504. | 6.06 |
| 44 | 3,4-Dimethoxy-N-(4-methoxy-benzyl)-N-phenyl-benzamide | 3,4-dimethoxy-N-phenyl-benzamide | 4-methoxybenzyl chloride | MH + 378.3 | 4.34 |
| 45 | 3,4-Dimethoxy-N-(3-methoxy-benzyl)-N-phenyl-benzamide | 3,4-dimethoxy-N-phenyl-benzamide | 3-methoxybenzyl chloride | MH + 378.3 | 4.41 |
| 46 | N-(3,4-Dichloro-benzyl)-3,4-dimethoxy-N-phenyl-benzamide | 3,4-dimethoxy-N-phenyl-benzamide | 3,5-dichlorobenzyl chloride | MH + 418.1, 416.2 | 5.59 |
| 47 | 3,4-Dimethoxy-N-naphthalen-2-ylmethyl-N-phenyl-benzamide | 3,4-dimethoxy-N-phenyl-benzamide | 2-(bromomethyl) naphthalene | MH + 398.3 | 5.25 |
| 48 | N-(4-tert-Butyl-benzyl)-3,4-dimethoxy-N-phenyl-benzamide | 3,4-dimethoxy-N-phenyl-benzamide | 4-(tert-butyl) benzyl bromide | MH + 404.3 | 6.02 |
| 49 | N-Biphenyl-2-ylmethyl-3,4-dimethoxy-N-phenyl-benzamide | 3,4-dimethoxy-N-phenyl-benzamide | 2-(bromomethyl) biphenyl | MH + 424.3 | 5.56 |
| 50 | N-(3,4-Dichloro-benzyl)-N-(2-methoxy-phenyl)-benzamide | N-(2-methoxyphenyl)-benzamide | 3,5-dichlorobenzyl chloride | MH + 388.2, 386.2 | 6.05 |
| 51 | N-(3,5-Di-tert-butyl-benzyl)-N-[4-(3-diethylamino-propyl)-phenyl]-benzamide | N-{4-[3-(diethylamino) propyl]phenyl}-benzamide | 3,5-bis(tert-butyl) benzyl bromide | MH + 513.4 | 4.69 |
| 52 | N-(3,5-Bis-trifluoromethyl-benzyl)-N-[4-(3-diethylamino-propyl)-phenyl]-benzamide | N-{4-[3-(diethylamino) propyl]phenyl}-benzamide | 3,5-bis (trifluouromethyl) benzyl bromide | MH + 537.3 | 3.71 |
| 53 | N-(3,5-Dibromo-benzyl)-N-[4-(3-diethylamino-propyl)-phenyl]-benzamide | N-{4-[3-(diethylamino) propyl]phenyl}-benzamide | 3,5-dibromobenzyl bromide | MH + 561.1, 559.1, 557,1 | 3.78 |
| 54 | N-[4-(3-Diethylamino-propyl)-phenyl]-N-(4-methoxy-benzyl)-benzamide | N-{4-[3-(diethylamino) propyl]phenyl}-benzamide | 4-methoxybenzyl chloride | MH + 431.3 | 2.62 |
| 55 | N-[4-(3-Diethylamino-propyl)-phenyl]-N-(3-methoxy-benzyl)-benzamide | N-{4-[3-(diethylamino) propyl]phenyl}-benzamide | 3-methoxybenzyl chloride | MH + 431.3 | 2.69 |

TABLE 1-continued

| Example No. | Name of Product | Reagent 1 | Reagent 2 | LCMS | LCMS RT, Minutes |
|---|---|---|---|---|---|
| 56 | N-(3,4-Dichloro-benzyl)-N-[4-(3-diethylamino-propyl)-phenyl]-benzamide | N-{4-[3-(diethylamino)propyl]phenyl}-benzamide | 3,5-dichlorobenzyl chloride | MH+ 471.2, 469.2 | 3.42 |
| 57 | N-[4-(3-Diethylamino-propyl)-phenyl]-N-naphthalen-2-ylmethyl-benzamide | N-{4-[3-(diethylamino)propyl]phenyl}-benzamide | 2-(bromomethyl) naphthalene | MH+ 451.3 | 3.21 |
| 58 | N-Biphenyl-2-ylmethyl-N-[4-(3-diethylamino-propyl)-phenyl]-benzamide | N-{4-[3-(diethylamino)propyl]phenyl}-benzamide | 2-(bromomethyl) biphenyl | MH+ 477.3 | 3.50 |
| 59 | 3-Methyl-thiophene-2-carboxylic acid (4-iodo-phenyl)-(5,5,8,8-tetramethyl-5,6,7,8-tetrahydro-naphthalen-2-ylmethyl)-amide | 2-[(2-pyridinylcarbonyl)amino]-benzoic acid, methyl ester | 6-chloromethyl-1,2,3,4-tetrahydo-1,1,4,4-tetramethyl naphthale | MH+ 544.1 | 10.68 |
| 60 | N-(4-Methoxy-benzyl)-N-phenyl-benzamide | benzanilide | 4-methoxybenzyl chloride | MH+ 318.3 | 4.82 |
| 61 | N-(3-Methoxy-benzyl)-N-phenyl-benzamide | benzanilide | 3-methoxybenzyl chloride | MH+ 318.3 | 4.90 |
| 62 | 3,4,5-Trimethoxy-N-naphthalen-2-ylmethyl-N-quinolin-3-yl-benzamide | 3,4,5-Trimethoxy-N-quinolin-3-yl-benzamide | 2-(bromomethyl) naphthalene | MH+ 479.2 | |
| 63 | N-(4-tert-Butyl-benzyl)-3,4,5-trimethoxy-N-quinolin-3-yl-benzamide | 3,4,5-Trimethoxy-N-quinolin-3-yl-benzamide | 4-(tert-butyl)benzyl bromide | MH+ 485.3 | |
| 64 | N-Biphenyl-2-ylmethyl-3,4,5-trimethoxy-N-quinolin-3-yl-benzamide | 3,4,5-Trimethoxy-N-quinolin-3-yl-benzamide | 2-(bromomethyl)biphenyl | MH+ 505.2 | |
| 65 | 3,4,5-Trimethoxy-N-(6-methoxy-pyridin-3-yl)-N-(5,5,8,8-tetramethyl-5,6,7,8-tetrahydro-naphthalen-2-ylmethyl)-benzamide | 3,4,5-Trimethoxy-N-(6-methoxy-pyridin-3-yl)-benzamide | 6-chloromethyl-1,2,3,4-tetrahydo-1,1,4,4-tetramethyl naphthale | MH+ 519.3 | |
| 66 | N-(3,5-Di-tert-butyl-benzyl)-3,4,5-trimethoxy-N-(6-methoxy-pyridin-3-yl)-benzamide | 3,4,5-Trimethoxy-N-(6-methoxy-pyridin-3-yl)-benzamide | 3,5-bis(tert-butyl) benzyl bromide | MH+ 521.3 | |
| 67 | N-(3,4-Dichloro-benzyl)-3,4,5-trimethoxy-N-(6-methoxy-pyridin-3-yl)-benzamide | 3,4,5-Trimethoxy-N-(6-methoxy-pyridin-3-yl)-benzamide | 3,5-dichlorobenzyl chloride | MH+ 479.1 | |
| 68 | 4-Isopropyl-N-pyridin-3-yl-N-(5,5,8,8-tetramethyl-5,6,7,8-tetrahydro-naphthalen-2-ylmethyl)-benzamide | p-isopropyl-N-3-pyridyl-benzamide | 6-chloromethyl-1,2,3,4-tetrahydo-1,1,4,4-tetramethyl naphthale | MH+ 441.6 | |
| 69 | 4-Isopropyl-N-(3-methoxy-benzyl)-N-pyridin-3-yl-benzamide | p-isopropyl-N-3-pyridyl-benzamide | 3-methoxybenzyl chloride | MH+ 361.3 | |
| 70 | 4-Isopropyl-N-naphthalen-2-ylmethyl-N-pyridin-3-yl-benzamide | p-isopropyl-N-3-pyridyl-benzamide | 2-(bromomethyl) naphthalene | MH+ 381.3 | |
| 71 | 'N-(4-tert-Butyl-benzyl)-4-isopropyl-N-pyridin-3-yl-benzamide | p-isopropyl-N-3-pyridyl-benzamide | 4-(tert-butyl) benzyl bromide | MH+ 387.3 | |
| 72 | N-Biphenyl-2-ylmethyl-4-isopropyl- | p-isopropyl-N-3-pyridyl-benzamide | 2-(bromomethyl) biphenyl | MH+ 407.3 | |

TABLE 1-continued

| Example No. | Name of Product | Reagent 1 | Reagent 2 | LCMS | LCMS RT, Minutes |
|---|---|---|---|---|---|
| | N-pyridin-3-yl-benzamide | | | | |
| 73 | 2-Ethoxy-N-pyridin-3-yl-N-(5,5,8,8-tetramethyl-5,6,7,8-tetrahydro-naphthalen-2-ylmethyl)-benzamide | 2-ethoxy-N-pyridin-3-yl-benzamide | 6-chloromethyl-1,2,3,4-tetrahydo-1,1,4,4-tetramethyl naphthale | MH + 443.3 | |
| 74 | N-(3,5-Di-tert-butyl-benzyl)-2-ethoxy-N-pyridin-3-yl-benzamide | 2-ethoxy-N-pyridin-3-yl-benzamide | 4-(tert-butyl) benzyl bromide | MH + 445.4 | |
| 75 | N-(3,5-Dibromo-benzyl)-2-ethoxy-N-pyridin-3-yl-benzamide | 2-ethoxy-N-pyridin-3-yl-benzamide | 3,5-dibromobenzyl bromide | MH + 493.0, 491.0, 489.0 | |
| 76 | 2-Ethoxy-N-(4-methoxy-benzyl)-N-pyridin-3-yl-benzamide | 2-Ethoxy-N-pyridin-3-yl-benzamide | 4-methoxybenzyl chloride | MH + 363.3 | |
| 77 | 2-Ethoxy-N-(3-methoxy-benzyl)-N-pyridin-3-yl-benzamide | 2-ethoxy-N-pyridin-3-yl-benzamide | 3-methoxybenzyl chloride | MH + 363.3 | |
| 78 | N-(3,4-Dichloro-benzyl)-2-ethoxy-N-pyridin-3-yl-benzamide | 2-ethoxy-N-pyridin-3-yl-benzamide | 3,5-dichlorobenzyl chloride | MH + 403.1, 401.1 | |
| 79 | 2-Ethoxy-N-naphthalen-2-ylmethyl-N-pyridin-3-yl-benzamide | 2-ethoxy-N-pyridin-3-yl-benzamide | 2-(bromomethyl) naphthalene | MH + 383.3 | |
| 80 | N-(4-tert-Butyl-benzyl)-2-ethoxy-N-pyridin-3-yl-benzamide | 2-ethoxy-N-pyridin-3-yl-benzamide | 4-(tert-butyl)benzyl bromide | MH + 389.3 | |
| 81 | N-Biphenyl-2-ylmethyl-2-ethoxy-N-pyridin-3-yl-benzamide | 2-ethoxy-N-pyridin-3-yl-benzamide | 2-phenylbenzyl bromide | MH + 409.3 | |
| 82 | N-(6-Butoxy-pyridin-3-yl)-2-diethylamino-N-(5,5,8,8-tetramethyl-5,6,7,8-tetrahydro-naphthalen-2-ylmethyl)-acetamide | N-(6-Butoxy-pyridin-3-yl)-2-diethylamino-acetamide | 6-chloromethyl-1,2,3,4-tetrahydo-1,1,4,4-tetramethyl naphthale | MH + 480.4 | |
| 83 | N-(6-Butoxy-pyridin-3-yl)-N-(4-tert-butyl-benzyl)-2-diethylamino-acetamide | N-(6-Butoxy-pyridin-3-yl)-2-diethylamino-acetamide | 4-(tert-butyl) benzyl bromide | MH + 426.4 | |
| 84 | 'N-Biphenyl-2-ylmethyl-N-(6-butoxy-pyridin-3-yl)-2-diethylamino-acetamide | N-(6-Butoxy-pyridin-3-yl)-2-diethylamino-acetamide | 2-(bromomethyl) naphthalene | MH + 446.3 | |
| 85 | N-(2-Methoxy-phenyl)-N-naphthalen-2-ylmethyl-benzamide | N-(2-methoxyphenyl)-benzamide | 2-(bromomethyl) naphthalene | MH + 368.3 | 5.63 |
| 86 | N-(4-Methoxy-benzyl)-N-(2-methoxy-phenyl)-benzamide | N-(2-methoxyphenyl)-benzamide | 4-methoxybenzyl chloride | MH + 348.3 | 4.79 |
| 87 | N-(3-Methoxy-benzyl)-N-(2-methoxy-phenyl)-benzamide | N-(2-methoxyphenyl)-benzamide | 3-methoxybenzyl chloride | MH + 348.3 | 4.83 |
| 88 | N-Biphenyl-2-ylmethyl-N-(2-methoxy-phenyl)-benzamide | N-(2-methoxyphenyl)-benzamide | 2-(bromomethyl) naphthalene | MH + 394.3 | 6.02 |
| 89 | N-[4-(3-Diethylamino-propyl)-phenyl]-N- | N-{4-[3-(diethylamino)propyl] phenyl}-benzamide | 6-chloromethyl-1,2,3,4-tetrahydo-1,1,4,4-tetramethyl | MH + 511.3 | 4.62 |

TABLE 1-continued

| Example No. | Name of Product | Reagent 1 | Reagent 2 | LCMS | LCMS RT, Minutes |
|---|---|---|---|---|---|
| | (5,5,8,8-tetramethyl-5,6,7,8-tetrahydro-naphthalen-2-ylmethyl)-benzamide | | naphthale | | |

LCMS = Liquid chromatography-mass spectrometry.
RT = Retention time.

TABLE 2

| Example No. | Names | Reagent 3 | Reagent 4 | LCMS | LCMS (RT) |
|---|---|---|---|---|---|
| 90 | N-Biphenyl-2-ylmethyl-2-ethoxy-N-(6-methoxy-pyridin-3-yl)-benzamide | N,N-3-(5-methoxypyridyl),2-phenylbenzylamine | 2-ethoxybenzoyl chloride | MH + 439.1 | 7.48A |
| 91 | N-Biphenyl-2-ylmethyl-2-methoxy-N-(6-methoxy-pyridin-3-yl)-benzamide | N,N-3-(5-methoxypyridyl),2-phenylbenzylamine | 2-methoxybenzoyl chloride | MH + 425.0 | 6.93A |
| 92 | N-Biphenyl-2-ylmethyl-2-methoxy-N-pyridin-3-ylmethyl-benzamide | N,N-3-methylpyridyl,2-phenylbenzylamine | 2-methoxybenzoyl chloride | MH + 409.1 | 3.21A |
| 93 | Benzo[b]thiophene-2-carboxylic acid biphenyl-2-ylmethyl-pyridin-4-yl-amide | N,N-4-pyridyl,2-phenylbenzylamine | benzo[b]thiophene-2-carbonyl chloride | MH + 421.0 | 6.41A |
| 94 | N-Biphenyl-2-ylmethyl-N-(6-methoxy-pyridin-3-yl)-2-nitro-benzamide | N,N-3-(5-methoxypyridyl),2-phenylbenzylamine | 2-nitrobenzoyl chloride | MH + 440.0 | 7.00A |
| 95 | N-Biphenyl-2-ylmethyl-4-ethoxy-N-(6-methoxy-pyridin-3-yl)-benzamide | N,N-3-(5-methoxypyridyl),2-phenylbenzylamine | 4-methoxybenzoyl chloride | MH + 439.1 | 7.70A |
| 96 | N-Biphenyl-2-ylmethyl-2-ethoxy-N-pyridin-3-ylmethyl-benzamide | N,N-3-methylpyridyl,2-phenylbenzylamine | 2-ethoxybenzoyl chloride | MH + 439.1 | 3.62A |
| 97 | Benzo[1,3]dioxole-4-carboxylic acid biphenyl-2-ylmethyl-pyridin-3-ylmethyl-amide | N,N-3-methylpyridyl,2-phenylbenzylamine | 2-Methylenedioxy benzoic acid chloride | MH + 423.0 | 3.18A |
| 98 | N-Biphenyl-2-ylmethyl-2-bromo-N-pyridin-3-ylmethyl-benzamide | N,N-3-methylpyridyl,2-phenylbenzylamine | 2-bromobenzoyl chloride | MH + 459.0, 457.0 | 3.57A |
| 99 | 3-Chloro-benzo[b]thiophene-2-carboxylic acid biphenyl-2-ylmethyl-pyridin-3-ylmethyl-amide | N,N-3-methylpyridyl,2-phenylbenzylamine | 3-Chloro-benzo[b]thiophene-2-carbonyl chloride | MH + 424.0 | 4.89A |
| 100 | N-Biphenyl-2-ylmethyl-2-nitro-N-pyridin-3-ylmethyl-benzamide | N,N-3-methylpyridyl,2-phenylbenzylamine | 2-nitrobenzoyl chloride | MH + 424.0 | 3.09A |
| 101 | 2-Benzyloxy-N-biphenyl-2-ylmethyl-N-pyridin-3-ylmethyl-benzamide | N,N-3-methylpyridyl,2-phenylbenzylamine | 2-benzyloxybenzoyl chloride | MH + 485.1 | 4.49A |
| 102 | N-Biphenyl-2-ylmethyl-4-ethoxy-N-pyridin-3-ylmethyl-benzamide | N,N-3-methylpyridyl,2-phenylbenzylamine | 4-ethoxybenzoyl chloride | MH + 423.1 | 3.72A |
| 103 | N-Biphenyl-2-ylmethyl-4-methoxy-N-(4-methoxy-phenyl)-benzamide | Biphenyl-2-ylmethyl-(4-methoxy-phenyl)-amine | 4-methoxybenzoyl chloride | MH + 424 | 7.40B |

TABLE 2-continued

| Example No. | Names | Reagent 3 | Reagent 4 | LCMS | LCMS (RT) |
|---|---|---|---|---|---|
| 104 | N-Biphenyl-2-ylmethyl-2-ethoxy-N-(4-methoxy-phenyl)-benzamide | Biphenyl-2-ylmethyl-(4-methoxy-phenyl)-amine | 2-ethoxybenzoyl chloride | MH + 438 | 7.56B |
| 105 | Benzo[1,3]dioxole-5-carboxylic acid biphenyl-2-ylmethyl-(4-methoxy-phenyl)-amide | Biphenyl-2-ylmethyl-(4-methoxy-phenyl)-amine | 2-Methylenedioxy benzoic acid chloride | MH + 438 | 7.21B |
| 106 | N-Biphenyl-2-ylmethyl-2,4-dimethoxy-N-(4-methoxy-phenyl)-benzamide | Biphenyl-2-ylmethyl-(4-methoxy-phenyl)-amine | 2,4-dimethoxybenzoyl chloride | MH + 454 | 7.10B |
| 107 | 2-Benzyloxy-N-biphenyl-2-ylmethyl-N-(4-methoxy-phenyl)-benzamide | Biphenyl-2-ylmethyl-(4-methoxy-phenyl)-amine | 2-Benzyloxy benzoyl chloride | MH + 500 | 8.09B |
| 108 | N-Biphenyl-2-ylmethyl-2-bromo-N-(4-methoxy-phenyl)-benzamide | Biphenyl-2-ylmethyl-(4-methoxy-phenyl)-amine | 2-bromobenzoyl chloride | MH + 474, 472 | 7.70B |
| 109 | Benzo[1,3]dioxole-4-carboxylic acid biphenyl-2-ylmethyl-(6-methoxy-pyridin-3-yl)-amide | N,N-3-(5-methoxypyridyl),2-phenylbenzylamine | 2-Methylenedioxybenzoic acid chloride | MH + 439 | 7.03A |

LCMS = Liquid chromatography-mass spectrometry.
RT = Retention time.
A = LCMS under Conditions A.
B = LCMS under Conditions B.

TABLE 3

| Example No. | Names | Reagent 5 | Reagent 6 | LCMS | LCMS (RT) |
|---|---|---|---|---|---|
| 110 | N-Biphenyl-2-ylmethyl-2-ethoxy-N-pyridin-2-yl-benzamide | N,N-2-pyridyl,2-phenylbenzylamine | 2-ethoxybenzoyl chloride | MH + 423.1 | 7.37 |
| 111 | N-Biphenyl-2-ylmethyl-2-bromo-N-pyridin-2-yl-benzamide | N,N-2-pyridyl,2-phenylbenzylamine | 2-bromobenzoyl chloride | MH + 445.0, 443.0 | 7.44 |
| 112 | N-Biphenyl-2-ylmethyl-2-nitro-N-pyridin-2-yl-benzamide | N,N-2-pyridyl,2-phenylbenzylamine | 2-nitrobenzoyl chloride | MH + 410.1 | 6.75 |
| 113 | 2-Benzyloxy-N-biphenyl-2-ylmethyl-N-pyridin-2-yl-benzamide | N,N-2-pyridyl,2-phenylbenzylamine | 2-benzyloxybenzoyl chloride | MH + 471.1 | 8.02 |
| 114 | N-Biphenyl-2-ylmethyl-2-bromo-N-pyridin-3-yl-benzamide | N,N-3-pyridyl,2-phenylbenzylamine | 2-bromobenzoyl chloride | MH + 445.0, 443.0 | 4.16 |
| 115 | 3-Chloro-benzo[b]thiophene-2-carboxylic acid biphenyl-2-ylmethyl-pyridin-3-yl-amide | N,N-3-pyridyl,2-phenylbenzylamine | 3-Chloro-benzo[b]thiophene-2-carbonyl chloride | MH + 445.0 | 5.37 |
| 116 | Benzo[b]thiophene-2-carboxylic acid biphenyl-2-ylmethyl-pyridin-3-yl-amide | N,N-3-pyridyl,2-phenylbenzylamine | benzo[b]thiophene-2-carbonyl chloride | MH + 421.1 | 4.86 |
| 117 | N-Biphenyl-2-ylmethyl-2-nitro-N-pyridin-3-yl-benzamide | N,N-3-pyridyl,2-phenylbenzylamine | 2-nitrobenzoyl chloride | MH + 410.0 | 3.69 |
| 118 | N-Biphenyl-2- | N,N-4-pyridyl,2- | 2-ethoxybenzoyl | MH + | 4.87 |

TABLE 3-continued

| Example No. | Names | Reagent 5 | Reagent 6 | LCMS | LCMS (RT) |
|---|---|---|---|---|---|
| | ylmethyl-2-ethoxy-N-pyridin-4-yl-benzamide | phenylbenzylamine | chloride | 409.1 | |
| 119 | N-Biphenyl-2-ylmethyl-2-methoxy-N-pyridin-4-yl-benzamide | N,N-4-pyridyl,2-phenylbenzylamine | 2-methoxybenzoyl chloride | MH + 395.1 | 4.28 |
| 120 | Benzo[1,3]dioxole-4-carboxylic acid biphenyl-2-ylmethyl-pyridin-4-yl-amide | N,N-4-pyridyl,2-phenylbenzylamine | 2-Methylenedioxy benzoic acid chloride | MH + 409.1 | 4.48 |
| 121 | N-Biphenyl-2-ylmethyl-2-bromo-N-pyridin-4-yl-benzamide | N,N-4-pyridyl,2-phenylbenzylamine | 2-bromobenzoyl chloride | MH + 445.0, 443.0 | 5.41 |
| 122 | N-Biphenyl-2-ylmethyl-2-nitro-N-pyridin-4-yl-benzamide | N,N-4-pyridyl,2-phenylbenzylamine | 2-nitrobenzoyl chloride | MH + 410.1 | 4.91 |
| 123 | 2-Benzyloxy-N-biphenyl-2-ylmethyl-N-pyridin-4-yl-benzamide | N,N-4-pyridyl,2-phenylbenzylamine | 2-benzyloxybenzoyl chloride | MH + 471.1 | 5.88 |
| 124 | N-Biphenyl-2-ylmethyl-4-ethoxy-N-pyridin-4-yl-benzamide | N,N-4-pyridyl,2-phenylbenzylamine | 4-ethoxybenzoyl chloride | MH + 409.1 | 4.33 |
| 125 | Benzo[b]thiophene-2-carboxylic acid biphenyl-2-ylmethyl-pyridin-3-ylmethyl-amide | N,N-3-methylpyridyl,2-phenylbenzylamine | benzo[b]thiophene-2-carbonyl chloride | MH + 435.1 | 5.08 |

LCMS = Liquid chromatography-mass spectrometry.
RT = Retention time.

TABLE 4

| Example No. | Names | Reagent 7 | Reagent 8 | LCMS | LCMS (RT) |
|---|---|---|---|---|---|
| 126 | N-Biphenyl-2-ylmethyl-N-(4-methoxy-phenyl)-2-methylsulfanyl benzamide | Biphenyl-2-ylmethyl-(4-methoxy-phenyl)-amine | 2-Methylsulfanyl-benzoyl chloride | MH + 440 | 6.81 |
| 127 | N-Biphenyl-2-ylmethyl-2-isopropylsulfanyl-N-(4-methoxy-phenyl)-benzamide | Biphenyl-2-ylmethyl-(4-methoxy-phenyl)-amine | 2-[(1-methylethyl)thio]-benzoyl chloride | MH + 468.1 | 7.54 |
| 128 | N-Biphenyl-2-ylmethyl-N-(3-methoxy-phenyl)-2-propylsulfanyl benzamide | Biphenyl-2-ylmethyl-(3-methoxy-phenyl)-amine | 2-(propylthio)-benzoyl chloride | MH + 468.0 | 7.57 |
| 129 | N-Biphenyl-2-ylmethyl-N-(3-methoxy-phenyl)-2-methylsulfanyl-benzamide | Biphenyl-2-ylmethyl-(3-methoxy-phenyl)-amine | 2-Methylsulfanyl-benzoyl chloride | MH + 440.0 | 6.88 |
| 130 | N-Biphenyl-2-ylmethyl-2-isopropylsulfanyl-N-(3-methoxy-phenyl)-benzamide | Biphenyl-2-ylmethyl-(3-methoxy-phenyl)-amine | 2-[(1-methylethyl)thio]-benzoyl chloride | MH + 468.1 | 7.61 |
| 131 | 2-Benzylsulfanyl-N-biphenyl-2-ylmethyl-N-(3-methoxy-phenyl)-benzamide | Biphenyl-2-ylmethyl-(3-methoxy-phenyl)-amine | 2-Benzylsulfanyl-benzoyl chloride | MH + 516.0 | 7.61 |
| 132 | 2-Benzylsulfanyl-N-biphenyl-2- | Biphenyl-2-ylmethyl-(4-chloro-phenyl)- | 2-Benzylsulfanyl-benzoyl chloride | MH + 520.0 | 8.20 |

TABLE 4-continued

| Example No. | Names | Reagent 7 | Reagent 8 | LCMS | LCMS (RT) |
|---|---|---|---|---|---|
| | ylmethyl-N-(4-chloro-phenyl)-benzamide | amine | | | |
| 133 | N-Biphenyl-2-ylmethyl-N-(3,4-dimethoxy-phenyl)-2-propylsulfanyl-benzamide | Biphenyl-2-ylmethyl-(3,4-dimethoxy-phenyl)-amine | 2-(propylthio)-benzoyl chloride | MH + 498.1 | 7.07 |
| 134 | N-Biphenyl-2-ylmethyl-N-(3,4-dimethoxy-phenyl)-2-methylsulfanyl-benzamide | Biphenyl-2-ylmethyl-(3,4-dimethoxy-phenyl)-amine | 2-Methylsulfanyl-benzoyl chloride | MH + 470.0 | 6.30 |
| 135 | N-Biphenyl-2-ylmethyl-N-(3,4-dimethoxy-phenyl)-2-isopropylsulfanyl-benzamide | Biphenyl-2-ylmethyl-(3,4-dimethoxy-phenyl)-amine | 2-[(1-methylethyl)thio]-benzoyl chloride | MH + 498.1 | 7.13 |
| 136 | N-Biphenyl-2-ylmethyl-N-(3,4-dimethoxy-phenyl)-3-phenylsulfanyl-benzamide | Biphenyl-2-ylmethyl-(3,4-dimethoxy-phenyl)-amine | 3-(phenylthio)-benzoyl chloride | MH + 532.0 | 7.43 |
| 137 | 2-Benzylsulfanyl-N-biphenyl-2-ylmethyl-N-(3,4-dimethoxy-phenyl)-benzamide | Biphenyl-2-ylmethyl-(3,4-dimethoxy-phenyl)-amine | 2-Benzylsulfanyl-benzoyl chloride | MH + 566.0 | 7.14 |

LCMS = Liquid chromatography-mass spectrometry.
RT = Retention time.

TABLE 5

| Example No. | Names | Reagent 9 | LCMS | LCMS (RT) |
|---|---|---|---|---|
| 138 | 'N-Biphenyl-2-ylmethyl-N-(4-methoxy-phenyl)-2-(propane-1-sulfinyl)-benzamide | N-Biphenyl-2-ylmethyl-N-(4-methoxy-phenyl)-2-propylsulfanyl-benzamide | MH+ 484 | 7.76 |
| 139 | 'N-Biphenyl-2-ylmethyl-N-(4-methoxy-phenyl)-2-(propane-2-sulfinyl)-benzamide | N-Biphenyl-2-ylmethyl-2-isopropylsulfanyl-N-(4-methoxy-phenyl)-benzamide | MH+ 484 | 7.64 |
| 140 | '2-Benzenesulfinyl-N-biphenyl-2-ylmethyl-N-(4-chloro-phenyl)-benzamide | N-Biphenyl-2-ylmethyl-N-(4-chloro-phenyl)-3-phenylsulfanyl-benzamide | MH+ 522, 524 | 8.58 |
| 141 | 'N-Biphenyl-2-ylmethyl-N-(3,4-dimethoxy-phenyl)-2-(propane-1-sulfinyl)-benzamide | N-Biphenyl-2-ylmethyl-N-(3,4-dimethoxy-phenyl)-2-propylsulfanyl-benzamide | MH+ 514 | 7.04 |
| 142 | N-Biphenyl-2-ylmethyl-N-(3,4-dimethoxy-phenyl)-2-(propane-2-sulfinyl)-benzamide | N-Biphenyl-2-ylmethyl-N-(3,4-dimethoxy-phenyl)-2-isopropylsulfanyl-benzamide | MH+ 514 | 6.93 |
| 143 | N-Bipbenyl-2-ylmethyl-N-(3,4-dimethoxy-phenyl)-2-phenylmethanesulfinyl- | 2-Benzylsulfanyl-N-biphenyl-2-ylmethyl-N-(3,4-dimethoxy-phenyl)-benzamide | MH+ 566 | 8.04 |

LCMS = Liquid chromatography-mass spectrometry.
RT = Retention time.

BIOLOGICAL METHODS

LPABC Screen

Purpose

The lipoprotein(a), [Lp(a)], biochemical coupling assay (LPABC) is used to characterize inhibitors of the apolipoprotein(a), [apo(a)], apolipoproteinB-100, [apoB-100], coupling reaction that generates Lp(a).

Protocol

Conditioned media from 293 cells (ATCC CRL-1573), permanently transfected with an apo(a) 17-kringle cDNA expression construct (pcDNA-AMP, In Vitrogen, Carlsbad, Calif.) using standard molecular biology techniques, was used as a source of recombinant apo(a) is diluted 1:3 with phosphate buffered saline (PBS) and 90 µL is pipetted into each well of a 96-well plate and placed into a 37° C. incubator for 10 minutes. Twenty microliters of a 0.3 to 50 µM solution of a compound of the present invention in PBS is added to the warmed plate. Ninety microliters of HepG2 (ATCC HB-8065) cell conditioned media diluted 1:3 with PBS is added to the apo(a)/compound mixture and mixed by pipetting up and down 5 times. The reaction is incubated for 67 minutes in a 37° C. incubator. A 100 µL aliquot of the reaction is removed and assayed for its Lp(a) content by an enzyme linked immunosorbent assay (ELISA).

LPA3 Screen

Purpose

The LPA3 screen is used to identify compounds that inhibit Lp(a) production. This screen employs permanently transfected HepG2 cells (HepG2$^{K17}$) that are generated using an apo(a) 17-kringle cDNA expression construct (pcDNA-AMP, In Vitrogen, Carlsbad, Calif.) in accordance with methods that are well-known in molecular biology.

Protocol

HepG2$^{K17}$ cells are seeded in 96-well plates at a density of 75,000 cells per well in 0.25 mL of Dulbecco's Modified Eagle Media (DMEM) containing 10% fetal bovine serum (FBS). Seeded plates are incubated overnight in a 37° C., 5% $CO_2$/95% $O_2$ incubator. The media is removed, replaced with (1) fresh media, or (2) fresh media plus 0.3 to 50 μM of a compound of the present invention in 20 μL of PBS, and the plates returned to the incubator for 8 hours. After the additional 8 hours of incubation, Lp(a) is assayed in the media by ELISA. Cells are digested with 0.5N NaOH overnight and assayed for total protein. Lp(a) values are normalized for total protein content.

TABLE 6

| Example No. | Lp ABC IC$_{50}$ μM | Lp A3 IC$_{50}$ μM |
|---|---|---|
| 40 | >50 | 60.4 |
| 41 | >50 | 49.3 |
| 42 | >50 | 70.8 |
| 43 | >50 | 31.6 |
| 44 | >50 | 51.4 |
| 45 | >50 | 52.1 |
| 46 | >50 | 35.1 |
| 47 | >50 | 17.3 |
| 48 | >50 | 30.9 |
| 49 | >50 | 14.0 |
| 50 | >50 | 15.0 |
| 51 | >50 | 24.5 |
| 52 | >50 | 12.0 |
| 53 | >50 | 14.6 |
| 54 | >50 | 41.6 |
| 55 | >50 | 37.0 |
| 56 | >50 | 11.0 |
| 57 | >50 | 11.4 |
| 58 | >50 | 11.6 |
| 59 | >50 | 41.1 |
| 60 | >50 | 28.8 |
| 61 | >50 | 47.1 |
| 62 | >50 | 22.2 |
| 63 | >50 | 25.1 |
| 64 | >50 | 13.1 |
| 65 | >50 | 32.6 |
| 66 | >50 | 19.7 |
| 67 | >50 | 54.6 |
| 68 | >50 | 39.8 |
| 69 | >50 | 18.8 |
| 70 | >50 | 7.2 |
| 71 | >50 | 43.0 |
| 72 | >50 | 37.1 |
| 73 | >50 | 10.0 |
| 74 | >50 | 11.6 |
| 75 | >50 | 14.9 |
| 76 | >50 | 33.3 |
| 77 | >50 | 44.5 |
| 78 | >50 | 10.3 |
| 79 | >50 | 17.0 |
| 80 | >50 | 19.2 |
| 81 | >50 | 0.9 |
| 82 | >50 | 36.8 |
| 83 | >50 | 34.0 |
| 84 | >50 | 43.7 |
| 85 | >50 | 10.2 |
| 86 | >50 | 30.1 |
| 87 | >50 | 19.2 |
| 88 | >50 | 16.5 |
| 89 | >50 | 13.2 |
| 90 | >50 | 31.7 |
| 91 | >50 | 46.5 |
| 92 | >50 | 6.3 |
| 93 | >50 | 10.5 |
| 94 | >50 | 24.8 |
| 95 | >50 | 11.4 |
| 96 | >50 | 7.5 |
| 97 | >50 | 7.8 |
| 98 | >50 | 8.5 |
| 99 | >50 | 24.7 |
| 100 | >50 | 45.8 |
| 101 | >50 | 10.8 |
| 102 | >50 | 15.9 |
| 103 | >50 | 49.0 |
| 104 | >50 | 11.9 |
| 105 | >50 | 13.4 |
| 106 | >50 | 9.3 |
| 107 | >50 | 15.4 |
| 108 | >50 | 37.7 |
| 109 | >50 | 11.8 |
| 110 | >50 | 14.0 |
| 111 | >50 | 18.7 |
| 112 | >50 | 23.7 |
| 113 | >50 | 25.1 |
| 114 | >50 | 26.7 |
| 115 | >50 | 23.5 |
| 116 | >50 | 9.3 |
| 117 | >50 | 18.0 |
| 118 | >50 | 5.8 |
| 119 | >50 | 4.8 |
| 120 | >50 | 18.1 |
| 121 | >50 | 3.8 |
| 122 | >50 | 22.4 |
| 123 | >50 | 2.3 |
| 124 | >50 | 3.3 |
| 125 | >50 | 23.9 |
| 126 | >50 | 16.0 |
| 127 | >50 | 49.4 |
| 128 | >50 | 46.8 |
| 129 | >50 | 6.5 |
| 130 | >50 | 31.4 |
| 131 | >50 | 40.1 |
| 132 | >50 | >74 |
| 133 | >50 | 16.7 |
| 134 | >50 | 12.9 |
| 135 | >50 | 21.9 |
| 136 | >50 | 33.8 |
| 137 | >50 | 9.8 |
| 138 | >15 | 7.0 |
| 139 | >15 | 3.5 |
| 140 | >15 | 24.9 |
| 141 | >50 | 6.0 |
| 142 | >50 | 7.0 |
| 143 | >15 | 1.6 |

What is claimed is:

1. A compound having the Formula I

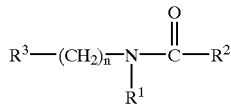

wherein $R^1$ is pyridyl, $CH_2$ pyridyl, or pyridyl substituted by $OC_1$–$C_6$alkyl;

n is 1 or 2;

$R^2$ is phenyl, substituted by $OC_1$–$C_6$alkyl,

Obenzyl-halogen or $NO_2$; and $R^3$ is 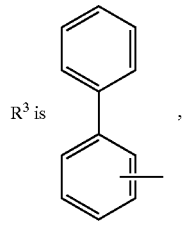

or phenyl substituted by $C_1$–$C_6$alkyl, or a pharmaceutically acceptable salt thereof.

2. A compound in accordance with claim 1 wherein $R^3$ is

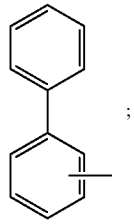

$R^2$ is ethoxy-phenyl; and $R^1$ is pyridyl.

3. A compound in accordance with claim 1 wherein $R^1$ is pyridyl.

4. The compounds:
N-(4-tert-Butylbenzyl)-2-ethoxy-N-pyridin-3-yl-benzamide; and
N-Biphenyl-2-ylmethyl-2-ethoxy-N-pyridin-3-yl-benzamide.

5. The compounds:
N-Biphenyl-2-ylmethyl-2-nitro-N-pyridin-3-ylmethyl-benzamide;
2-Benzyloxy-N-biphenyl-2-ylmethyl-N-pyridin-3-ylmethyl-benzamide;
N-Biphenyl-2-ylmethyl-4-ethoxy-N-pyridin-3-ylmethyl-benzamide;
Benzo[1,3]dioxole-4-carboxylic acid biphenyl-2-ylmethyl-(6-methoxy-pyridin-3-yl)-amide.

6. The compounds:
N-Biphenyl-2-ylmethyl-2-ethoxy-N-pyridin-2-yl-benzamide;
N-Biphenyl-2-ylmethyl-2-bromo-N-pyridin-2-yl-benzamide;
N-Biphenyl-2-ylmethyl-2-nitro-N-pyridin-2-yl-benzamide;
2-Benzyloxy-N-piphenyl-2-ylmethyl-N-pyridin-2-yl-benzamide;
N-Biphenyl-2-ylmethyl-2-bromo-N-pyridin-3-yl-benzamide;
N-Biphenyl-2-ylmethyl-2-nitro-N-pyridin-3-yl-benzamide;
N-Biphenyl-2-ylmethyl-2-ethoxy-N-pyridin-4-yl-benzamide; and
N-Biphenyl-2-ylmethyl-2-methoxy-N-pyridin-4-yl-benzamide.

7. The compounds:
Benzo[1,3 dioxole-4-carboxylic acid biphenyl-2-ylmethyl-pyridin-4-yl-amide;
N-Biphenyl-2-ylmethyl-2-bromo-N-pyridin-4-yl-benzamide;
N-Biphenyl-2-ylmethyl-2-nitro-N-pyridin-4-yl-benzamide;
2-Benzyloxy-N-biphenyl-2-ylmethyl-N-pyridin-4-yl-benzamide; and
N-Biphenyl-2-ylmethyl-4-ethoxy-N-pyridin-4-yl-benzamide.

8. A pharmaceutical composition comprising a compound of claim 1 in ad-mixture with a pharmaceutically acceptable carrier.

* * * * *